United States Patent [19]

Murray et al.

[11] Patent Number: 5,051,518

[45] Date of Patent: Sep. 24, 1991

[54] PHARMACOLOGICALLY ACTIVE 2- AND 3-SUBSTITUTED (1',5'-DIARYL-3-PYRAZOLYL)-N-HYDROXY-PROPANAMIDES

[75] Inventors: William V. Murray, Belle Mead; Michael P. Wachter, Bloomsbury, both of N.J.

[73] Assignee: Ortho Pharmaceutical Corporation, Raritan, N.J.

[21] Appl. No.: 534,325

[22] Filed: Jun. 4, 1990

Related U.S. Application Data

[63] Continuation of Ser. No. 181,035, Apr. 27, 1988, abandoned, which is a continuation-in-part of Ser. No. 55,806, May 29, 1987, abandoned.

[51] Int. Cl.[5] .............................................. C07D 231/12

[52] U.S. Cl. ...................................... 548/373; 548/378

[58] Field of Search .......................................... 548/373

[56] References Cited

U.S. PATENT DOCUMENTS

| | | | |
|---|---|---|---|
| 3,896,143 | 7/1975 | Kathawala | 548/378 |
| 4,042,706 | 8/1977 | Ahrens et al. | 514/406 |

*Primary Examiner*—Robert W. Ramsuer

[57] ABSTRACT

2- and 3-substituted (1',5'-diaryl-3'-pyrazolyl)-N-hydroxypropanamides, a method for their preparation, compositions containing the same and methods of their use are disclosed. The N-hydroxypropanamides are useful in alleviating inflammatory and cardiovascular disorders in mammals.

3 Claims, No Drawings

PHARMACOLOGICALLY ACTIVE 2- AND 3-SUBSTITUTED (1',5'-DIARYL-3-PYRAZOLYL)-N-HYDROXY-PROPANAMIDES

CROSS-REFERENCE TO RELATED APPLICATIONS

This is a continuation of application Ser. No. 181,035, filed Apr. 27, 1988 now abandoned, which is a continuation-in-part of Ser. No. 55,806, filed May 29, 1987 now abandoned.

DESCRIPTION

1. Technical Field

The present invention relates to 2- and 3-substituted pyrazole propionic acid derivatives, and particularly to N-hydroxy, N-alkyl pyrazole propanamide analogs of these compounds which are pharmacologically active in alleviating inflammation, asthma, hypersensitivity, myocardial ischemia, dermatological conditions such as psoriasis, dermatitis and gastrointestinal inflammatory conditions such as inflammatory bowel syndromes, and to a method for synthesizing those pyrazole derivatives.

2. Background

Nonsteroidal anti-inflammatory drugs (NSAID's) such as indomethacin, naproxen, ibuprofen, tolectin, fenoprofen and the like have generally been shown to attenuate the biosynthesis of prostaglandins by inhibiting the activity of the enzyme cyclooxygenase. The prostaglandin end-products of the cyclooxygenase pathway are responsible for many of the early signs of inflammation including hyperalgesia, increases in vascular permeability leading to edema, and pyrexia. The activity and potency of the NSAID's in reducing these signs and symptoms is, for the most part, correlated with their ability to inhibit prostaglandin biosynthesis.

The other major pathway of arachidonic acid metabolism is the lipoxygenase pathway. Lipoxygenase products of arachidonate metabolism, the leukotrienes, hydroxyeicosatetraenoic acids (HETES) and hydroperoxyeicosatetraenoic acids (HPETES), have been shown or implicated to be involved in disease states including acute and chronic inflammation, arthritis, allergic and other hypersensitivity disorders, dermatological diseases such as psoriasis, acne, atopic dermatitis, contact sensitivity, eczema and others, cardiovascular disorders secondary to myocardial ischemia or infarction, thromboembolism or vasculitis or platelet aggregation, and hyperalgesic disorders, gynecological disorders such as dysmenorrhea, ocular inflammation, sperm motility or function, and others.

Leukotriene $B_4$ ($LTB_4$), another product of the lipoxygenase pathway, as well as HETES and HPETES can mediate induction of other phlogistic substances such as thromboxanes and prostacyclin, is chemotactic to inflammatory cells, and is hyperalgesic. Many of these mediators have been identified in skin, lungs, coronary circulation, eyes, gastrointestinal tract and other organs, and in the synovial fluid of rheumatoid arthritic patients. In chronic inflammatory conditions such as rheumatoid arthritis, it is believed to be the chronic influx of leukocytes, probably mediated by $LTB_4$, that is the eventual cause of joint erosion.

It is believed that inhibitors of the lipoxygenase pathway could lead to a relatively permanent effect on inflammatory disorders such as rheumatoid arthritis since they could modulate the actual mechanisms of tissue and joint breakdown. Similarly, drugs that could inhibit prostaglandin synthesis via the cyclooxgenase pathway could modulate and reduce early manifestations of inflammation. Pharmacologically active compounds that can inhibit both enzyme pathways at similar concentrations (dual inhibitors) provide a more complete relief for patients suffering from arthritis, hypersensitivity, dermatological, cardiovascular, gastrointestinal, ocular, and gynecological disorders than present drugs that inhibit one pathway, but not the other as is the case for usually used NSAID's that are predominantly inhibitors of the cyclooxygenase (prostaglandin synthesis) pathway.

A number of 1,5-diaryl-3-substituted pyrazoles are reported in the literature. Some of those pyrazoles have been reported to have pharmacological activity.

For example Fulmer et al., *J. Het. Chem.*, 17:799–800 (1980) report the synthesis of 1,3,5-triaryl pyrazoles, as do Foote et al., *J. Het. Chem.*, 7:89–92 (1970), Beam et al., *J. Het. Chem.*, 9:183–185 (1972); Soliman et al., *J. Pharm. Sci.*, 70:606–610 (1981), and Barluenga et al., *J.C.S. Chem. Comm.*, 891 (1979). Soliman et al., *J. Pharm. Sci.*, 70:602–605 (1981) also report synthesis of 3-methyl-1,5-diarylpyrazoles in which the 1-position aryl is a phenylsulfonylurea or thiourea. Of the above reports, only the two reports by Soliman et al. discuss any pharmacological activity for the pyrazoles prepared or for analogs of those pyrazoles, and those materials are reported to have hypoglycemic activity.

Virmani et al., *Indian J. Chem., Sect.* B. 17B: 472–477 (1979) report the synthesis of 3-omega-alkylaminoalkyl pyrazoles among other compounds. The 1,5-diaryl-3-substituted pyrazoles reported contained a phenyl group at the 1-position, a 4-nitrophenyl at the 5-position, and a $(CH_2)_n$—$NHCH_3$ group at the 3-position, where n is 3,4 or 5 (3–5). This report stated that the compounds prepared were screened for a number of biological activities, with nine of the ninety-four numbered compounds synthesized having mild anti-inflammatory activity, two others having diuretic activity and two others having weak anti-cancer activity. The above-discussed 1,5-diaryl-3-substituted pyrazoles were not among the compounds reported to have any pharmacological activity.

Vereshchagin et al., *Zh. Oro. Khim.*, 7:907–912 (1971) reported the synthesis of 1,5-diaryl-3-substituted pyrazoles. The 3-substituents were reported to be alkoxy alkylene in which the alkoxy radical was methoxy or phenoxy and the alkylene was methylene or isopropylene, while the 1,5-diaryl radicals were unsubstituted phenyl.

Jahn and Wagner-Jauregg, *Arzneim-Forsch.* (*Drug Res.*). 24:494–499 (1974) reported the synthesis and some pharmacological activities of 1,5-diaryl-3-substituted-4,5-dihydropyrazoles. The aryl group at the 1-position for each reported compound was phenyl, while the 5-aryl substituent was reported to be phenyl, 4-methoxyphenyl, 3-methoxy-4-hydroxyphenyl, and 2-hydroxyphenyl. The before-mentioned pyrazoles were substituted at the 3-position by bonding to the 3-position of propionic acid or propiohydroxamic acid. These compounds were said to possess antirheumatic activity.

Shawali et al., *J. Het. Chem.*, 3:989–92 (1976); Shawali, *J. Het. Chem.*, 14:375–81 (1977); and Matsumoto et al., *Bull. Chem. Soc. Japan*, 47:946–949 (1979) reported the synthesis of 1,5-diaryl-3-subsituted pyrazoles, all of which also included a substituent other than hydrogen at the 4-position on the pyrazole ring. Exemplary 4-position substituents were reported to include cyano, amino, carboethyoxy, and phenylcarbonyl. These reports included no mention of biological activity of the compounds reported.

A series of benzimidoylpyrazoles was reported by Shrof et al., *J. Med. Chem.*, 24:1521-1525 (1981). These compounds were reported to possess activities of sulfonyl urea and biguanide hypoglcemics.

Biere et al., *Arch. Phar.*, 316:608-616 (1983) reported the synthesis of 1,4-diaryl-pyrazole-3-acetic acid derivatives, some of which also contained an aryl substituent at the 5-position. The synthesized compounds were assayed for use as anti-inflammatory drugs in rats. The compounds assayed that also contained 5-position substituents were reported to be relatively inactive.

A further group of 1,5-diphenyl-4-substituted-pyrazole-3-acetic acids was reported by El-Sayed and Ohta, *Bull. Chem. Soc. Japan*, 4:1801-1803 (1973). Those compounds were utilized as intermediates in the synthesis of pyrazolo-[4,3-c]-pyridines. Another group of 1,5-diphenyl-4-substituted-pyrazoles, some of which also include methyl, phenyl and carboxymethyl groups at the 3-position, was reported in Al-Saleh et al., *J.C.S. Perkin I*, 642-645 (1981). The reports of El-Sayed and Ohta and those of Al-Saleh et al. make no mention of the pharmacological properties of the pyrazole derivatives reported. Another group of 1,5-diaryl-3,4-disubstituted pyrazoles and 4,5-dihydro-5-hydroxy pyrazoles was reported in Fusco and Croce, *Gazz. Chim. Ital.*, 101:703-272 (1971).

SUMMARY OF THE INVENTION

In copending application Ser. No. 867,996, a series of 1,5-substituted pyrazoles is described in which the side chain on the pyrazole ring is unsubstituted.

The present invention relates to 2- and 3-substituted (1',5'-diaryl-3'-pyrazolyl)-propionic acid derivatives, their use and methods of synthesis. The compounds of the present invention are pharmacologically active in alleviating inflammation, and inhibit the cyclooxygenase enzyme pathway, the lipoxygenase enzyme pathway, or preferably both pathways.

In particular, the invention contemplates a substituted pyrazole compound having a structure that conforms to formula I or II.

I

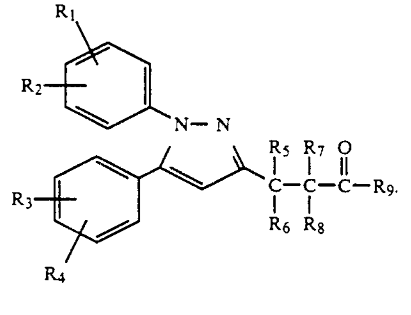

-continued

II

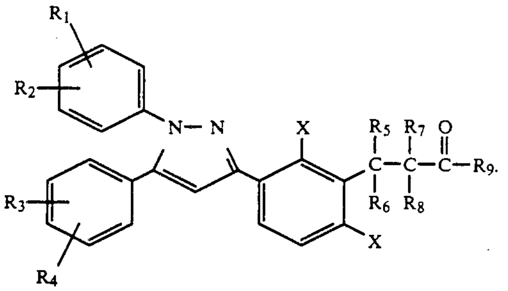

wherein $R_1$, $R_2$, $R_3$ and $R_4$ are the same or different and are individually selected from the group consisting of hydrogen, lower alkyl, lower alkoxy, amino, acetamido, phenyl, halo, hydroxy, lower alkylsulfonyl, lower alkylthio, nitro, trifluoromethyl, ω-trifluoromethyl lower alkoxy or where $R_1$, $R_2$ or $R_3$, $R_4$ taken together with the phenyl group to which they are attached, form a naphthyl or substituted naphthyl group;

$R_5$, $R_6$, $R_7$ and $R_8$ are the same or different and are hydrogen or lower alkyl; $R_5$, $R_6$ or $R_7$, $R_8$ may also form part of a spirocycloalkyl ring having 5-7 carbon atoms: $R_5$, $R_6$, $R_7$ and $R_8$ when taken together may form part of an aryl ring or a heterocyclic ring such as a phenyl ring or a pyridyl ring; $R_6$ and $R_8$ when taken together may form part of a ring selected from the group consisting of a cyclohexyl, cyclohexenyl and a 7-oxabicyclo[2.2.1]heptenyl ring; $R_9$ is selected from hydroxy, $—OR_{10}$ or $—N(OH)R_{10}$ wherein $R_{10}$ is lower alkyl; and the side chain $—CR_5R_6CR_7R_8C(O)R_9$ may be $—CH_2CH(aryl)C(O)R_9$ wherein the aryl group is selected from phenyl and substituted phenyl wherein the substituent is lower alkoxy, dilower alkoxy, phenyl, carboxymethyl and carboxy, biphenyl, naphthyl and heterocycloaryl such as pyridyl or $CH(aryl)CH_2C(O)R_9$ wherein the aryl group is selected from phenyl and substituted phenyl wherein the substitutent is halo, lower alkyl or lower alkoxy, biphenyl, naphthyl and heterocycloaryl such as pyridyl; provided that at least one of $R_5$, $R_6$, $R_7$ and $R_8$ in Formula I is other than hydrogen. In Formula II, X is lower alkoxy, $R_5$, $R_6$, $R_7$ and $R_8$ are hydrogen and $R_9$ hydroxy, $—OR_{10}$ or $—N(OH)R_{10}$ wherein $R_{10}$ is lower alkyl.

In preferred practice, $R_1$ and $R_2$ are lower alkoxy having 1-4 carbon atoms or hydrogen, and $R_3$ and $R_4$ are selected from the group consisting of halo, trifluroromethyl, lower alkyl and lower alkoxy.

The present invention also contemplates a pharmaceutical composition that comprises an anti-inflammatory amount of an above-described N-hydroxypropanamide compound dispersed in a pharmaceutically acceptable carrier. The dose may be administered by topical, p.o., parenteral or aerosol routes. In preferred practice, the substituted N-hydroxypropanamide compound is capable of inhibiting both the cyclooxygenase and the lipoxygenase pathways in the amount present in the composition, when the composition is introduced into a mammal.

Further contemplated is a method for alleviating inflammation in a mammal exhibiting an inflammatory condition. That method comprises administering to that mammal a pharmaceutical composition that includes as the active ingredient an effective amount of an above-described N-hydroxypropanamide compound dispersed in a pharmaceutically acceptable carrier for topical, oral, parenteral and aerosol administration.

A method for synthesizing a 1',5'-diaryl-3-pyrazolyl-N-hydroxypropanamide is also contemplated.

The present invention provides several benefits and advantages.

A particular benefit of the invention is that it provides pharmacologically active compounds that are useful in treating inflammatory conditions.

Another benefit of the present invention is that some of its pharmacologically active compounds inhibit the cyclooxygenase enzyme pathway, thereby providing a further means for studying that biological process.

Another advantage of the present invention is that some of its pharmacologically active compounds inhibit the lipoxygenase enzyme pathway, thereby providing a further means for studying that biological process.

Still further benefits and advantages of the present invention will be apparent to those skilled in the art from the detailed description and Examples that follow.

DETAILED DESCRIPTION OF THE INVENTION

1',5'-Diaryl-3-pyrazolyl-N-hydroxypropanamide compounds, pharmaceutical compositions containing a substituted propanamide compound as an active ingredient, a method of treating a mammal exhibiting an inflammatory condition and a method of synthesizing the substituted propanamide compound are contemplated herein.

In the above formula, $R_1$, $R_2$, $R_3$ and $R_4$ are substituents on phenyl rings that substitute for hydrogen atoms at positions 1 and 5 of the pyrazole ring. It is preferred that at least one of $R_1$ and $R_2$, and one of $R_3$ and $R_4$ be substituted at the 4-positions of their respective phenyl rings.

In examining the above structural formula to which the useful N-hydroxypropanamide compounds conform, it is noted that the $R_1$, $R_2$, $R_3$ and $R_4$ radicals can be a "lower" alkyl, "lower" alkoxy and the like. Groups and radicals referred to as "lower" denote that they possess 1 to about 6 carbon atoms. The same is true for "lower" groups and radicals that are sustituents of the "lower" groups and radicals enumerated.

Lower alkyl radicals include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, and the like.

Lower alkoxy radicals are oxygen ethers formed from a before-described lower alkyl group. Exemplary radicals include methoxy, ethoxy, propoxy, isopropoxy, n-butoxy, and the like.

Lower alkylthio radicals of $R_1$,$R_2$,$R_3$ and $R_4$ are sulfide ethers and are thus analogous to the oxygen ethers described above.

Halo radicals preferably include chloro and bromo, as well as fluoro and iodo.

Lower alkylsulfonyl radicals contain a before-described lower alkyl radical bonded to an $SO_2$ moiety that is itself also bonded to a phenyl ring. Exemplary lower alkylsulfonyl radicals thus include methylsulfonyl, ethylsulfonyl, 2-ethylbutylsulfonyl and the like.

An omega-trifluoromethyl lower alkoxy radical is a lower alkoxy radical as before described that additionally includes a trifluoromethyl group at a position farthest on the alkyl chain from the place of bonding to the phenyl ring. Exemplary of such radicals are the 2,2,2-trifluoromethylethoxy.

Naphthyl and substituted naphthyl radicals can replace an aryl group herein at either the 1- or 2-positions to provide 1-naphthyl or 2-naphthyl substituents, respectfully. Substituents on the naphthyl radicals can be any of those described herein as being useful aryl substituents. Exemplary substituted 1- and 2-naphthyls include 6-methoxy-2-naphthyl and the like.

The compounds of structure I in which $R_9$ is O-lower alkyl are synthesized by addition of the appropriately substiuted 3-bromomethyl-1,5-diphenylpyrazole A to the anion of the appropriately substituted aryl ester B generated by treatment with sodium hydride in a suitable solvent such as dimethylformamide according to Scheme 1 ($R_7$=Aryl)

SCHEME 1

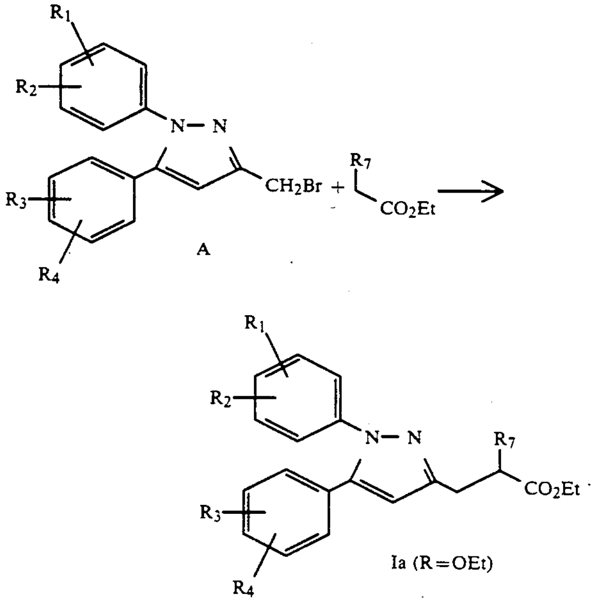

A

Ia (R=OEt)

The 3-bromomethylpyrazole A is synthesized as depicted in Scheme 2. The 4-aryl-2,4-dioxobutanoate D is synthesized by treatment of the anion of acetophenone C with a dialkyl oxalate such as diethyl oxalate and then converted to the 3-carboalkoxypyrazole E with the appropriately substitued phenylhydrazine. Reduction with $LiAlH_4$ gave the corresponding hydroxymethyl analog which was then converted to the bromomethylpyrazole A with phosphorus tribromide.

SCHEME 2

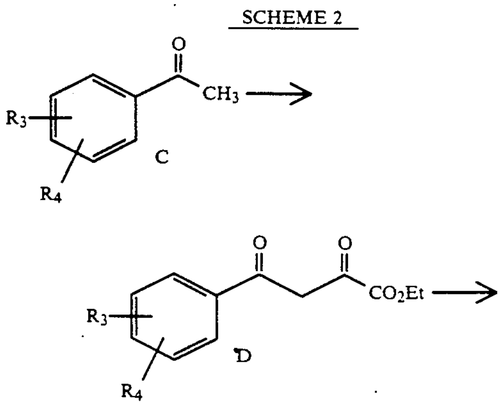

C

D

-continued

SCHEME 2

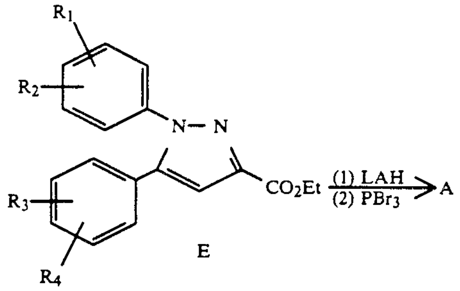

E

The compounds of Structure I in which $R_9$ is hydroxy and N(OH)Me are synthesized as shown in Scheme 3. Hydrolysis of the ester with aqueous base such as sodium or potassium hydroxide gives the pyrazole propionic acid ($R_9$=OH) which upon treatment with oxalyl chloride in a suitable solvent such as $CH_2Cl_2$, for example, affords the corresponding acyl chloride which is then converted with an N-alkylhydroxylamine such as N-methylhydroxylamine to the hydroxamic acid ($R_9$=N(OH)$R_{10}$ where $R_{10}$ is lower alkyl).

SCHEME 3

Ia ($R_4$ = OEt) —Base→ Ia ($R_4$ = OH) —(1) ClCOCOCl (2) $CH_3NHOH$→

-continued

SCHEME 3

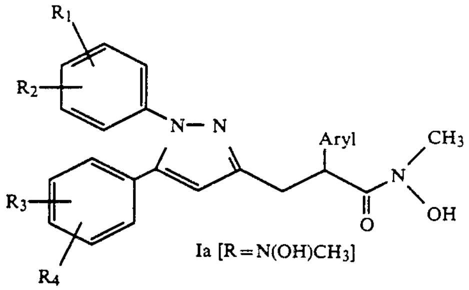

Ia [R=N(OH)$CH_3$]

The compounds of Structure Ib in which $R_5$, $R_6$ or $R_7$, $R_8$ is a spiroalkyl group are synthesized by the route shown in Scheme 4. Treatment of the anion of the appropriately substituted acetophenone C with a cycloalkyl-1-carboxy-1-acetic acid anhydride F (n=1-3) affords a mixture of 2- and 3-spiroalkyl diketohexanoic acids G and H from which the major isomer G is isolated by chromatography or recrystallization. Treatment of G with the appropriately substituted phenylhydrazine gives the 2-cycloalkylsubstituted pyrazole propionic acid which is then converted to hydroxamic acid Ib by the standard procedure and separated from the corresponding 1,3-diphenyl pyrazole isomer by chromatography and recrystallation.

SCHEME 4

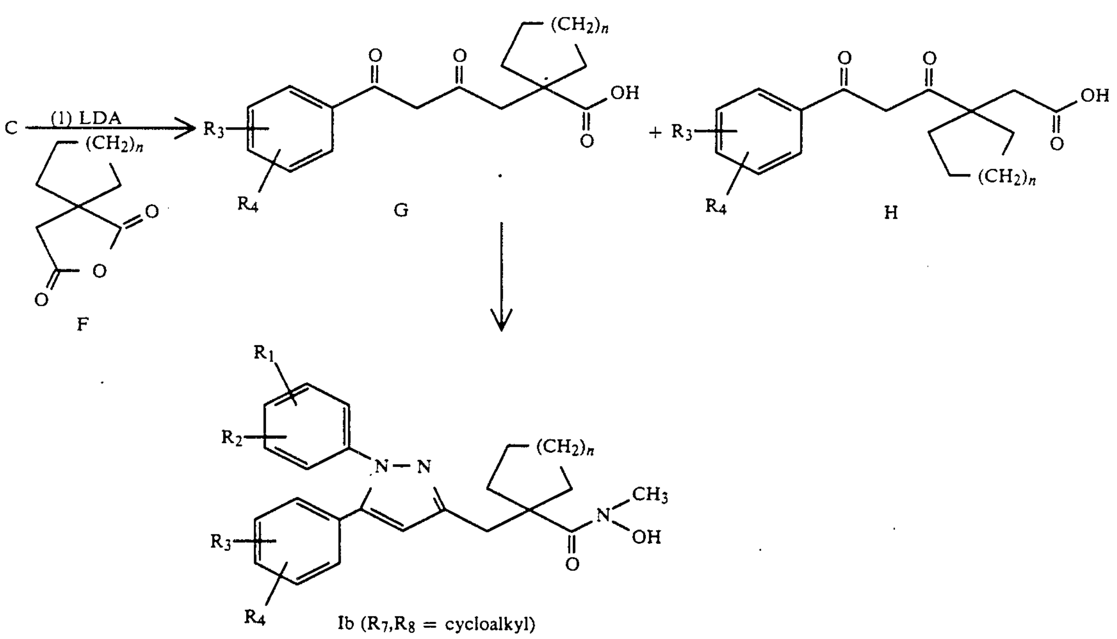

C, F, G, H

Ib ($R_7$,$R_8$ = cycloalkyl)

The compounds of Structure Ic in which $R_5$, $R_6$ or $R_7$ $R_8$ are each lower alkyl such as dimethyl are synthesized from diketo acids J and K in a similar manner to the spirocycloalkyl analogs above as shown in Scheme 5 for the dimethyl case.

SCHEME 5

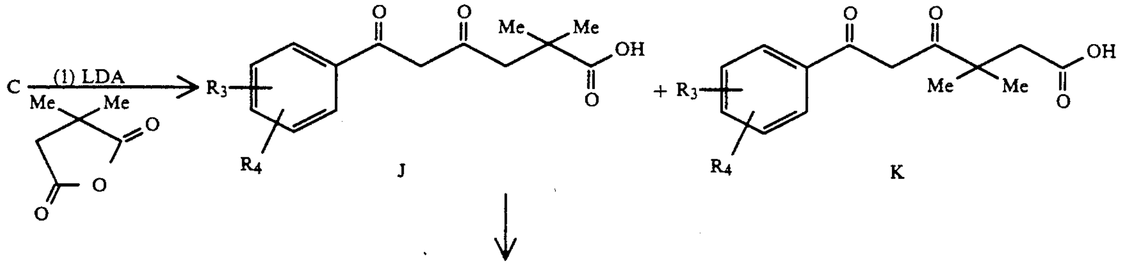

J
K
Ic ($R_7$,$R_8$ = Methyl)

Those compounds of structure Ic in which either $R_5$ or $R_7$ is lower alkyl were synthesized by treatment of the anion of ketone C with the appropriately substituted butyrolactone L to give the corresponding 1-aryl-1,3-dioxohexanol M which is condensed with the appropriate phenylhydrazine to afford pyrazole alcohol N and its 1,3-isomer. The isomers can be separated by chromatography. Oxidation with a suitable oxidizing agent such as, for example, Jones reagent to the propionic acid followed by hydroxamic acid formation by the above described procedure gives Ic. Scheme 6 illustrates this process when $R_5$ is methyl.

SCHEME 6

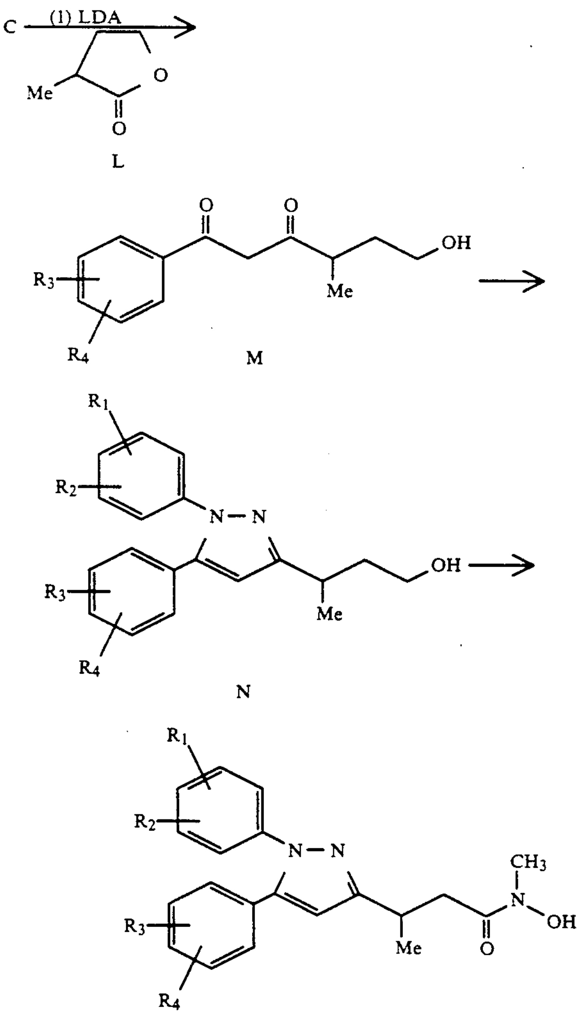

L
M
N
Ic ($R_5$ = Methyl)

Alternatively, the compounds of Structure Ic in which either $R_5$ or $R_7$ is lower alkyl such as methyl, for example, may be synthesized by the method shown in Scheme 5 by treatment of the anion of ketone C with 4-methylsuccinic anhydride, separation of the isomeric diketo acids by chromatography and subsequent conversion to the pyrazole derivatives.

The compounds having an aryl, cycloalkyl or heterocyclic ring in the side chain are synthesized by treatment of the anion of acetophenone C with the appropriate bicyclic anhydride O to afford diketo acid P which is then transformed to the hydroxamic acid by the methods described above. Scheme 7 depicts the synthesis of these compounds when the bicyclic anhydride is phthalic anhydride.

SCHEME 7

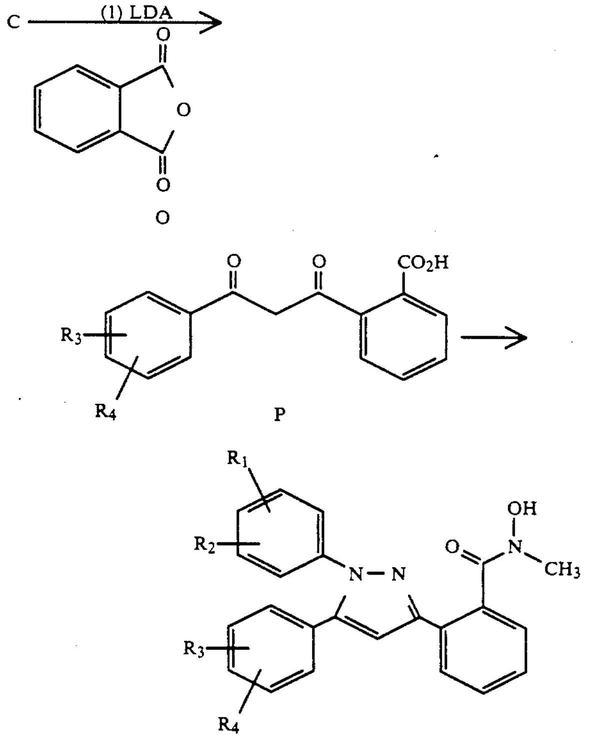

O
P
Ic ($R_5$-$R_8$ = Phenyl)

The compounds of Structure Ia' in which $R_9$ is O-lower alkyl are synthesized as shown in Scheme 8. The hydroxymethyl pyrazole derivative, synthesized as described in Scheme 2 from compound E, is oxidized to aldehyde U with a suitable oxidizing agent such as, for example, $CrO_3$ in pyridine. Treatment of the aldehyde with the appropriately substituted Grignard reagent V affords the alcohol W which is then oxidized with a suitable oxidizing agent such as, for example, pyridinium chlorochromate to the ketone X. A modified Wittig reaction of the ketone X with triethyl phosphonoacetate gives the ethyl pyrazole cinnamates Y as a mixture of E and Z isomers which can be separated by chromatography or reduced directly by catalytic hydrogenation with Pd/C to the propanoate Ia'. The esters can also be prepared from the corresponding pyrazole propionic acids by esterification with an esterifying agent such as diazomethane, for example.

The compounds of Structure Ia' in which $R_9$ is hydroxy and N(OH)Me are synthesized using the identical steps shown in Scheme 3 for the corresponding derivatives of Structure Ia.

Additional aryl derivatives were synthesized by treatment of aldehyde U with an arylmagnesium halide or with an aryl halide or activated aryl derivative such as 2-methoxybenzene and butyllithium at −78° C. to give alcohol W'. Subsequent conversion to Y' was carried out as described in Scheme 8. Compounds of Structure Y' were converted to the unsaturated acids A' and subsequently to the hydroxamic acids B' following the procedures described for the 2-aryl derivatives shown in Scheme 2. The overall scheme for the conversion of U to B' is depicted in Scheme 8'. Aryl derivatives synthesized include phenyl, substituted phenyl, biphenylyl, naphthyl, substituted naphthyl, and heterocyclic aryl such as thienyl and furyl.

SCHEME 8

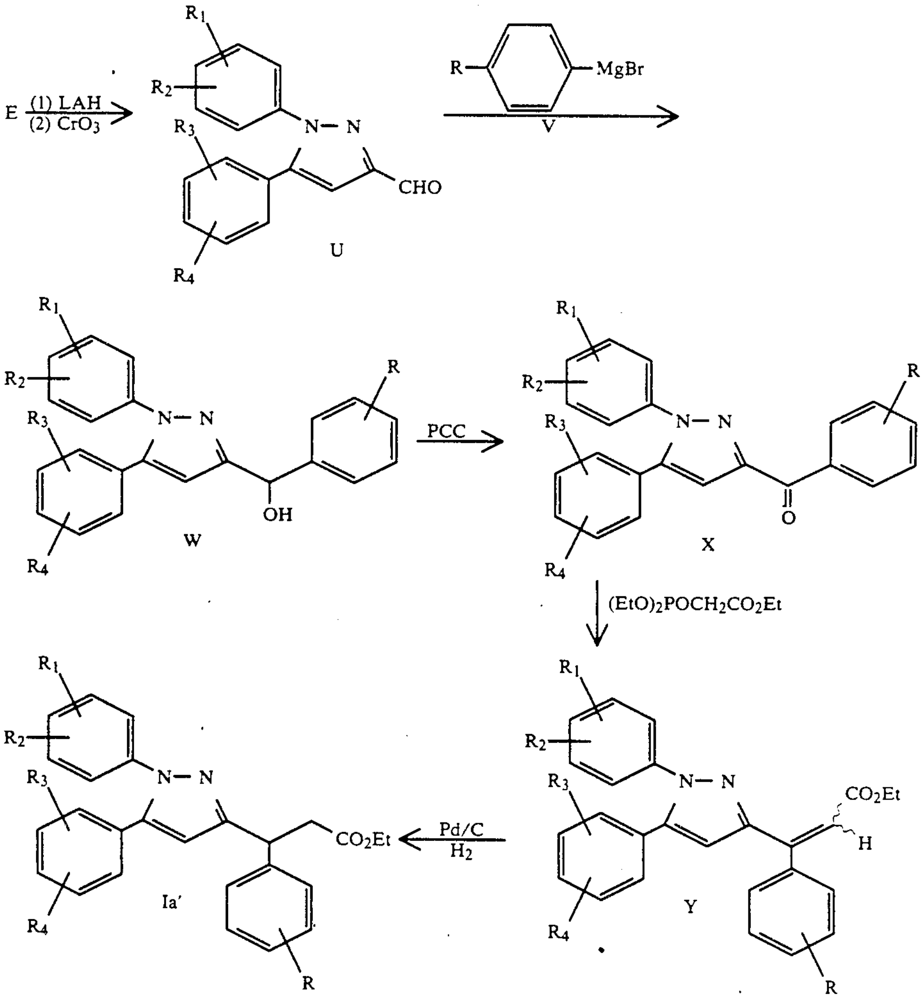

SCHEME 8'

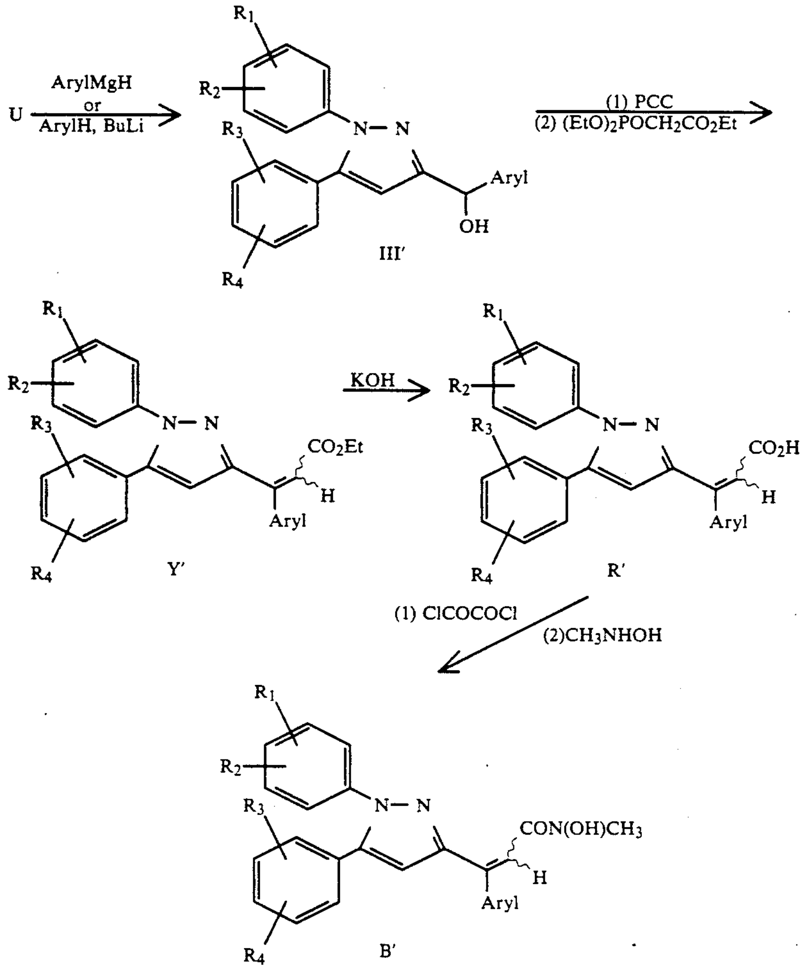

III'

Y'

R'

B'

The compounds of Structure II are synthesized by the route shown in Scheme 9. Alkylation of dihydroxyacetophenone Q with an alkylating agent such as methyl iodide, for example, with a base such as potassium carbonate in a suitable solvent such as acetone gives the corresponding 2,4-dialkoxy analog which upon treatment with the appropriate phenylhydrazine affords the hydrazone R. Formation of the dianion of R with a base such as butyl lithium followed by treatment with the appropriately substituted benzoate ester such as methyl 4-chlorobenzoate gives pyrazole S. Hydroboration of the terminal double bond with borane-methyl sulfide complex afforded the primary alcohol T which was transformed to hydroxamic acid II by the procedures described in Scheme 6.

SCHEME 9

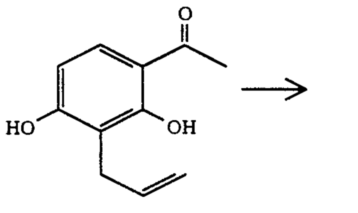

Q

-continued

SCHEME 9

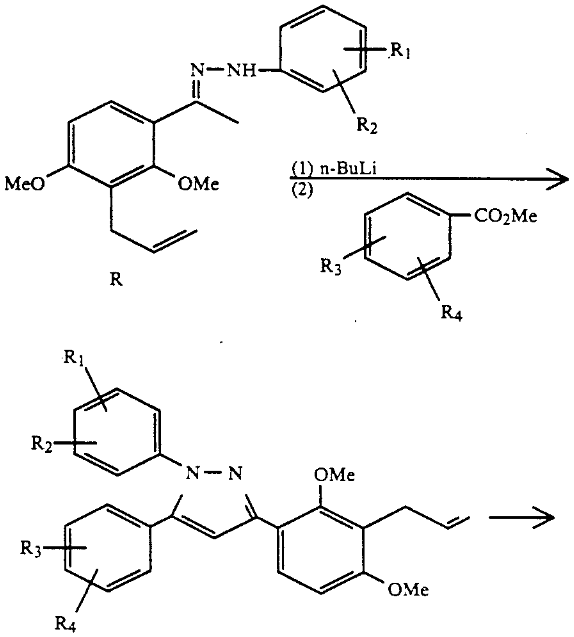

R

S

-continued
SCHEME 9

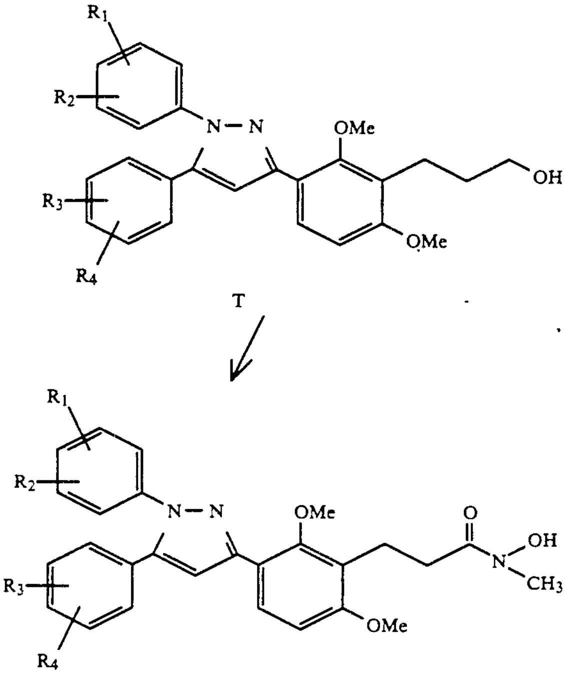

II

The intermediates used in the preparation of the N-hydroxypropanamides are also novel compounds and are included as part of the present invention. Basic salts of those carboxylic and hydroxamic acids are also contemplated, and are formed by treatment of the acid with an appropriate, non-toxic, pharmaceutically acceptable alkaline reagent to form a carboxylate or hydroxamate cation salt. Exemplary non-toxic, pharmaceutically acceptable cation salts of such carboxylic and hydroxamic acids include sodium, potassium, zinc, aluminum, calcium and magnesium. These salts also readily form in aqueous solutions of the carboxylic and hydroxamic acids.

Specific, particularly preferred compounds of this invention are named hereinbelow, followed by a parenthesized, underlined numeral for ease of identification and correlation with the syntheses and anti-inflammation study described in detail hereinafter.

The preferred species of this invention include:

1. Ethyl 3-[5-(4-chlorophenyl)-1-(4-methoxyphenyl)-3-pyrazolyl-2-phenylpropanoate (8);

2. 3-[5-(4-chlorophenyl)-1-(4-methoxyphenyl)-3-pyrazolyl]-2-(4 -chlorophenyl)-N-hydroxy-N-methylpropanamide(26);

3. 3-[5-(4-chlorophenyl)-1-(4-methoxyphenyl)-3-pyrazolyl]-N-hydroxy-2 -spirocycloheptyl-N-methylpropanamide (42);

4. 3-[5-(4-chlorophenyl)-1-(4-methoxyphenyl)-3-pyrazolyl]-2, N-dimethyl-N-hydroxypropanamide (52);

5. 2-[5-(4-chlorophenyl)-1-(4-methoxyphenyl)pyrazolyl-3-yl]-N-hydroxy-N-methylbenzamide hemihydrate (62);

6. cis-2-[5-(4-chlorophenyl)-1-(4-methoxyphenyl)-3-pyrazolyl]-1-(N-hydroxy-N-methyl)carboxamidocyclohexane (63);

7. 3-[3-[5-(4-chlorophenyl)-1-(4-methoxyphenyl)-pyrazol-3-yl]-2,6 -dimethoxyphenyl]-N-hydroxy-N-methylpropanamide (75).

8. [1,5-Bis(4-methoxyphenyl)-3-pyrazolyl]-1-phenylmethanol (105).

9. 1-(4-Methoxyphenyl)-3-(4-methylbenzoyl)-5-(4-methylphenyl)pyrazole (109).

10. (Z)-Ethyl 3-[1(4-methoxyphenyl)-5-(4-methylphenyl)-3-pyrazolyl]-3-(4 -methylphenyl)propenoate (125).

11. 3-(4-Fluorophenyl)-3-[1-(4-methoxyphenyl)-5-(4-methylphenyl)-3-pyrazolyl] propanoic acid (151).

12. (E)-3-[1-(4-Methoxyphenyl)-5-(4-methylphenyl)-3-pyrazolyl]-3-phenyl-2 -propenoic acid (155).

13. (E)-3-(4-Chlorophenyl)-3-[1-(4-methoxyphenyl)-5-(4-methylphenyl)-3-pyrazolyl]propenoic acid (157).

14. (Z)-3-(4-Chlorophenyl)-3-[1-(4-methoxyphenyl)-5-(4-methylphenyl)-3 -pyrazoly]propenoic acid (158).

15. (E)-3-(4-Fluorophenyl)-N-hydroxy-3-[1-(4-methoxyphenyl)-5-(4 -methylphenyl)-3-pyrazolyl]-N-methylpropenamide (163).

A pharmaceutical composition that comprises an anti-inflammatory amount of a compound of this invention dispersed in a pharmaceutically acceptable carrier is also contemplated herein. The composition comprises a unit dosage of the substituted pyrazole compound.

The substituted N-hydroxypropanamide compounds of this invention are capable of inhibiting the lipoxygenase enzyme pathway and/or the cyclooxygenase (prostaglandin synthetase) enzyme pathway. In preferred practice, the substituted N-hydroxy compound of the pharmaceutical composition is capable of inhibiting both the lipoxyenase and the cyclooxygenase enzyme pathways in the amount at which that substituted pyrazole compound is present in the pharmaceutical composition, when that composition is introduced as a unit dose into an appropriate mammal such as a laboratory rat.

The term "unit dosage" and its grammatical equivalent is used herein to refer to physically discrete units suitable as unitary dosages for human patients and other warm blooded animals, each unit containing a predetermined effective, pharmacologic amount of the active ingredient calculated to produce the desired pharmacological effect in association with the required physiologically tolerable carrier, e.g., a diluent or a vehicle. The specifications for the novel unit dosage forms of this invention are dictated by and are directly dependent on (a) the unique characteristics of the active ingredient, and (b) the limitations inherent in the art of compounding such an active ingredient for therapeutic use in humans and other animals. Examples of suitable unit dosage forms in accord with this invention are tablets, capsules, pills, powder packets, granules, wafers, and the like, segregated multiples of any of the foregoing, as well as liquid solutions and suspensions.

The active ingredient is referred to herein as being dispersed in the carrier. Thus, the dispersion formed can be a simple admixture, a non-settling dispersion as in the case of certain emulsions, or as an ultimate dispersion, a true solution.

The amount of active ingredient that is administered in vivo depends on the age and weight of the mammal treated, the particular medical condition to be treated, the frequency of administration, and the route of administration. The dose range can be about 0.01 to about 500 milligrams per kilogram of body weight, more preferably about 0.1 to about 50 milligrams per kilogram of body weight and most preferably about 0.1 to about 25 milligrams per kilogram of body weight. The human adult dose is in the range of about 10 to about 2000 milligrams daily, given as a single dose or in 3 or 4 divided doses. Veterinary dosages correspond to human dosages with the amounts administered being in proportion to the weight of the animal as compared to adult humans.

As is seen from the data discussed hereinafter, orally administered unit doses containing about 1 to about 50 milligrams of a 2- and 3-substituted (1',5'-diaryl-3'-pyrazolyl)-N-hydroxypropanamide per kilogram of laboratory rat body weight (e.g., about 200 grams each) were useful in reducing inflammation. These results are contrary to those reported by Virmani et al., *Indian J. Chem., Sect. B.* 17:472–477 (1979) who reported compounds that are structurally similar to those described herein were not active as anti-inflammatory agents.

Physiologically tolerable carriers are well known in the art. Exemplary of liquid carriers are aqueous solutions that contain no materials in addition to the substituted pyrazole compound, or contain a buffer such as sodium phosphate at physiological pH value, saline and the like.

Liquid compositions can also contain liquid phases in addition to and to the exclusion of water. Exemplary of such additional liquid phases are glycerin and vegetable oils such as cottonseed oil.

Exemplary solid carriers (diluents) include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Antioxidants such as methylparaben and propylparaben can be present in both solid and liquid compositions, as can sweeteners such a cane or beet sugar, sodium saccharin, sodium cyclamate and the dipeptide methyl ester sweeteneer sold under the trademark NUTRASWEET (aspartame) by G. D. Searle Co.

A method for alleviating inflammation in a mammal exhibiting an inflammatory condition is also contemplated. The method comprises administering to that mammal an effective amount of a pharmaceutical composition that includes a unit dose of an active ingredient that is the before-described substituted N-hydroxypropanamide compound dispersed in a pharmaceutically acceptable carrier. The pharmaceutical composition is preferably maintained within the mammal until the substituted N-hydroxypropanamide compound is cleared from the mammal's body by natural means such as excretion or metabolism.

The pharmaceutical composition can be administered orally, topically or by injection, by means well known in the art. In preferred practice, the composition is admininstered orally as a tablet, capsule or aqueous dispersion.

BEST MODES FOR CARRYING OUT THE INVENTION

Melting points (mp) were determined on a Thomas-Hoover apparatus, and are uncorrected. Nuclear magnetic resonance (NMR) spectra for hydrogen atoms were measured in the indicated solvent with tetramethylsilane (TMS) as the internal standard on a Varian T-60A or an IBM WP-100 spectrometer. The values are expressed in parts per million downfield from TMS. EI and CI mass spectra were obtained on a Finnigan 1015D quadrupole mass spectrometer coupled to a Finnigan 9500 gas chromatograph or a Finnigan MAT 8230 Double Focusing high resolution mass spectrometer. In Tables 1–4 the elemental analysis for each compound was within ±0.4%.

EXAMPLE 1

Ethyl 5-(4-chlorophenyl)-1-(4-methoxyphenyl)pyrazole-3-carboxylate (1)

Ethyl 4-(4-chlorophenyl)-2,4-dioxobutanoate sodium salt (10.0 g, 36.1 mM), synthesized from 4-chloroacetophenone and diethyloxalate employing lithium diisopropylamide as base, and 4-methoxyphenylhydrazine hydrochloride (6.31 g, 36.1 mM) in cold absolute EtOH (360 ml) were stirred at 0° for 4 hr., at rt for 18 hr and then at reflux for 5 hr. The resulting solution was evaporated in vacuo, $H_2O$ (100 ml) was added and the aqueous phase extracted with $Et_2O$ (3×100 ml). The combined ether layer was washed (brine), dried ($Na_2SO_4$) and concentrated in vacuo to give a crude solid which by NMR was a 5:1 mixture of the title compound to the corresponding 1,3-diphenyl pyrazole. Recrystallization from EtOAc:hexane (2×) afforded pure 1 (7.93 g, 61%) as a white solid, mp=107°–108° C., MS, (DCI) m/e 357 (M+1).

Ethyl 4-(4-methoxyphenyl)-2,4-dioxobutanoate lithium salt (60.0 g, 0.23 M) synthesized from 4-methoxyacetophenone and diethyloxalate employing lithium hexamethyldisilazide as base, and 4-methoxyphenylhydrazine hydrochloride (44 g, 0.25 M) were combined in ethanol (2 1) and stirred at RT for 24 hr, concentrated in vacuo and crystallized to afford ethyl 1,5-bis (4-methoxyphenyl)pyrazole-3-carboxylate as a white solid, 75 g, 91% yield; mp=97°–98° C.; MS, (m/e) 352 (M+).

Anal. Calcd. for $C_{20}H_{20}N_2O_4$: C, 68.17; H, 5.72; N, 7.95

Found: C, 68.39; H, 5.75; N, 7.87.

EXAMPLE 2

Ethyl 1-(4-methoxyphenyl)-5-(4-methylphenyl)pyrazole-3-carboxylate (2)

Following the procedure of Example 1, but substituting 4'-methylacetophenone for 4-chloroacetophenone afforded the title compound 2 as a white solid, mp=124°–125°, MS, (DCI) m/e 337 (M+1).

Anal. Calcd. for $C_{20}H_{20}N_2O_3$: C, 71.41; H, 5.99; N, 8.33

Found: C, 71.13; H, 6.16; N, 8.36

EXAMPLE 3

5-(4-Chlorophenyl)-3-hydroxymethyl-1-(4-methoxyphenyl) pyrazole (3)

A solution of compound 1 (9.1 g, 25.5 mM) in THF (50 ml) was added over 45 min to a stirred suspension of $LiAlH_4$ (0.726 g, 19.1 mM) in THF (50 ml) at 0° C. and stirring continued for 1 hr. The suspension was diluted with $Et_2O$ (100 ml) and $H_2O$ (0.73 ml), 15% aq. NaOH (0.73 ml) and $H_2O$ (2.1 ml) were added in sequence. The mixture was stirred for 16 hr, $MgSO_4$ added and the suspension stirred an additional hour, filtered and the solids washed with $Et_2O$. The combined organic layer was concentrated in vacuo, the residue dissolved in hot EtOAc and crystallized by the addition of hexane to give pure 3 (7.43 g, 93%) as a white solid, mp 95°–97° C., MS, m/e 314 (M+).

Anal.Calcd.for $C_{17}H_{15}ClN_2O_2$: C, 64.87; H, 4.88; N, 8.90

Found: C, 64.75; H, 4.83; N, 8.84.

Following the procedure of Example 3, but substituting ethyl 1,5-bis(4- methoxyphenyl)pyrazole-3-carboxylate for compound 1 afforded 3-hydroxymethyl-1,5-bis(4-methoxyphenyl)pyrazole (88) as a yellow foam, MS, (m/e) 310 (M+).

Anal. Calcd. for $C_{18}H_{18}N_2O_3 \cdot \frac{1}{4}H_2O$: C, 68.88; H, 5.94; N, 8.93

Found: C, 68.75; H, 6.01; N, 8.88

EXAMPLE 4

3-Hydroxymethyl-1-(4-methoxyphenyl)-5-(4-methylphenyl) pyrazole (4)

Following the procedure for Example 3, but substituting compound 2 for compound 1 afforded the title compound 4 as a white solid, mp=100°-102° C., MS, m/e 294 (M+).

Anal. Calcd. for $C_{18}H_{18}N_2O_2$: C, 73.45; H, 6.16; N, 9.52

Found: C, 73.24; H, 6.16; N, 9.57

EXAMPLE 5

3-Bromomethyl-5-(4-chlorophenyl)-1-(4-methoxyphenyl) pyrazole (5)

To a solution of compound 3 (3.14 g, 10 mM) in benzene (100 ml) was added $PBr_3$ (1.35 g, 5 mM) in benzene (10 ml) dropwise with stirring. The reaction mixture was refluxed 1 hr, cooled, poured into ice water (100 ml) and extracted with $Et_2O$ (2×100 ml). The combined organic layer was washed with 10% $NaHCO_3$, dried ($Na_2SO_4$), filtered and concentrated to give a tan oilwhich crystallized on standing to afford compound 5, mp=88°-90° C., MS, (DCI) m/e 377 (M+1).

EXAMPLE 6

3-Bromomethyl-1-(4-methoxyphenyl)-5-(4-methylphenyl) pyrazole (6)

Following the procedure of Example 5, but substituting compound 4 for compound 3 afforded the title compound 6 which was recrystallized from $CH_2Cl_2$:hexane as a white solid, mp=119°-121° C.

Anal. Calcd. for $C_{18}H_{17}BrN_2O$: C, 60.52; H, 4.80; N, 7.84

Found: C, 60.61; H, 4.97; N, 7.57

EXAMPLE 7

Ethyl 3-[5-(4-Chlorophenyl)-1-(4-methoxyphenyl)-3-pyrazolyl]-2-(4 -chlorophenyl)propanoate (7)

NaH (3.12 g, 60% suspension in mineral oil, 78 mM) was suspended in anhydrous DMF (150 ml), cooled to 0° C. and ethyl 4-chlorophenyl acetate (15.5 g, 78 mM) in DMF (150 ml) was added dropwise and the resulting solution stirred for 1 hr. Pyrazole bromide 5 (8.0 g, 21 mM) in DMF (150 ml) was added dropwise and the resulting reaction mixture allowed to warm to rt. The solvent was evaporated in vacuo, the residue dissolved in EtOAc (200 ml), washed with $H_2O$ (4×100 ml), dried ($Na_2SO_4$) and evaporated in vacuo to give a residue which was purified by flash chromatography on silica using 20% EtOAc:hexane as eluent to afford the title compound 7 as a yellow glass, 7.48 g (72% yield), MS, m/e 494 (M+).

Anal.Calcd.for $C_{27}H_{24}Cl_2N_2O_3$: C,65.46; H, 4.88; N, 5.65

Found: C,65.18; H, 4.90; N, 5.49

Following the procedure of Example 7, and using either pyrazole bromide 5 or 6 and substituting the appropriate aryl acetate for ethyl 4-chlorophenyl acetate afforded the compounds of Table 1.

TABLE 1

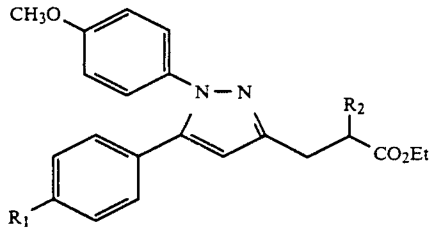

| Comp. No. | $R_1$ | $R_2$ | % Yield | MS m/e ($M^+$) | C,H,N |
|---|---|---|---|---|---|
| 8 | Cl | Phenyl | 45 | 460 | X |
| 9 | Cl | 3,4-dimethoxyphenyl | 52 | 520 | X |
| 10 | Cl | 4-methoxyphenyl | 34 | 490 | X |
| 11 | $CH_3$ | 2-naphthyl | 30 | 490 | X |
| 12 | $CH_3$ | 1-naphthyl | 33 | 490 | X |
| 13 | $CH_3$ | 2-methoxyphenyl | 61 | 470 | X |
| 14 | $CH_3$ | 2-pyridyl | 49 | 441 | X |
| 15 | $CH_3$ | 4-biphenyl | 31 | 516 | X |
| 16* | $CH_3$ | 2-carboxymethylphenyl | 92 | 484 | X |
| 17 | $CH_3$ | 3-pyridyl | 61 | 441 | X |

*Synthesized as the methyl ester rather than as the ethyl ester

EXAMPLE 8

3-[5-(4-Chlorophenyl)-1-(4methoxyphenyl)-3-pyrazolyl-2-(4-chlorophenyl) propanoic acid (18)

Compound 7 (7 g, 14.1 mM) was dissolved in a solution of 50% aq. KOH (4.74 g, 42.3 mM) in absolute EtOH (200 ml) and refluxed for 1.5 hr. The solvent was removed in vacuo and the solid residue dissolved in $H_2O$ (250 ml), acidified to pH 4 with 4N HCl and extracted with EtOAc (300 ml). The organic layer was dried ($Na_2SO_4$), filtered and evaporated in vacuo to give a foam which was crystallized from $CH_2Cl_2$:hexane to give the title compound 18 (6.6 g) as a white solid, mp=161.5°-163° C., MS, m/e 466 ($M^+$).

Anal. Calcd. for $C_{25}H_{20}Cl_2N_2O_3$: C, 64.25; H, 4.31; N, 5.99

Found: C, 64.43; H, 4.33; N, 5.70

Following the procedure of Example 8, but substituting the compounds of Table 1 for compound 7 gave the compounds of Table 2.

TABLE 2

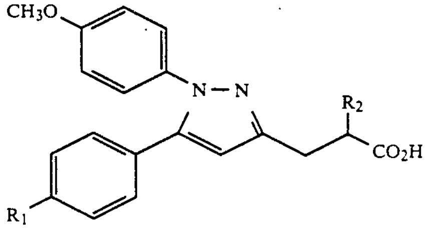

| Comp. No. | $R_1$ | $R_2$ | Melting Point | MS m/e ($M^-$) | C, H,N |
|---|---|---|---|---|---|
| 19 | Cl | 4-methoxyphenyl | 193-195° | 462 | X |
| 20 | Cl | 3,4-dimethoxyphenyl | 109-115° | 492 | X |

TABLE 2-continued

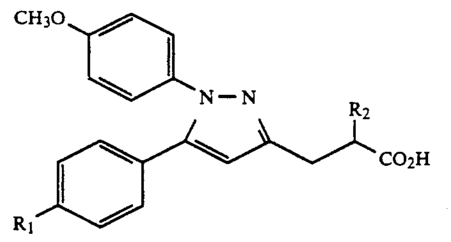

| Comp. No. | $R_1$ | $R_2$ | Melting Point | MS m/e ($M^+$) | C, H,N |
|---|---|---|---|---|---|
| 21 | $CH_3$ | 2-naphthyl | 158-159.5° | 462 | X |
| 22* | $CH_3$ | 1-naphthyl | >280° | 418 (M-44) | X |
| 23 | $CH_3$ | 2-methoxyphenyl | 150-151° | 442 | X |
| 24 | $CH_3$ | 4-biphenyl | 167-170° | 488 | X |
| 25** | $CH_3$ | 2-carboxyphenyl | 204.5-205.5° | 438 (M-18) | X |

*Isolated as the sodium salt
**Prepared from compound 16

EXAMPLE 9

3-[5-(4-Chlorophenyl)-1-(4-methoxyphenyl)-3-pyrazolyl]-2-(4 -chlorophenyl)-N-hydroxy-N-methylpropanamide (26)

Compound 18 (1.77 g, 3.8 mM) was suspended in $CH_2Cl_2$ (80 ml) and treated with oxalyl chloride (0.45 ml, 5.2 mM) to give a clear yellow solution which was allowed to reflux for 1 hr. The solvent was evaporated in vacuo to give the acyl chloride as a white semi-solid which was dissolved in $CH_2Cl_2$ (15 ml) and added dropwise to a solution of N-methylhydroxylamine•HCl (0.48 g, 5.7 mM), $Et_3N$ (2.12 ml, 15.2 mM) and $CH_2Cl_2$ (15 ml) which was cooled to 0° C. The reaction was allowed to warm to rt and was stirred for 12 hours, washed with 5% aq. HCl (50 ml), dried ($Na_2SO_4$) and evaporated to give a crude semi-solid which was purified by flash chromatography on Silica (40% EtOAc:-hexane) followed by recrystallization from $CHCl_2$:hexane to give the title compound 26 (1.15 g, 61%) as a white solid, mp=113°-117° C., MS, m/e 496 ($M^+$).

Anal. Calcd. for $C_{26}H_{23}Cl_2N_3O_3$: C,62.91;H,4.67;N,8.47

Found: C,62.50;H,4.48;N,8.32

Following the procedure of Example 9, but substituting the compounds of Table 2 for compound 18 gave the compounds of Table 3.

TABLE 3

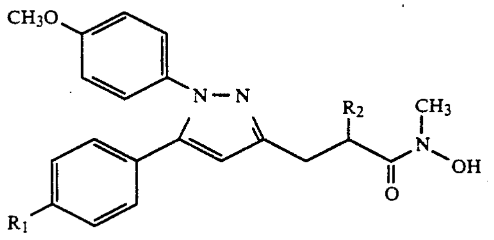

| Comp. No. | $R_1$ | $R_2$ | Melting Point | MS m/e ($M^+$) | C,H,N |
|---|---|---|---|---|---|
| 27 | Cl | phenyl | 154-156° | 461 | X |
| 28 | Cl | 3,4-dimethoxyphenyl | 160-164° | 521 | X* |
| 29 | Cl | 4-methoxyphenyl | 158-159.5° | 491 | X |
| 30 | $CH_3$ | 2-naphthyl | 173-175° | 491 | X |

TABLE 3-continued

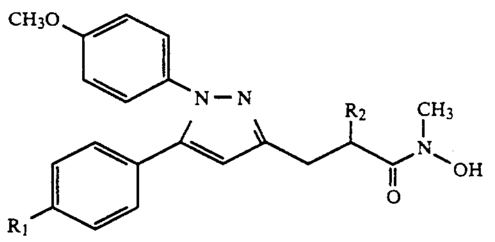

| Comp. No. | $R_1$ | $R_2$ | Melting Point | MS m/e ($M^+$) | C,H,N |
|---|---|---|---|---|---|
| 31 | $CH_3$ | 1-naphthyl | 140-142° | 491 | X** |
| 32 | $CH_3$ | 2-methoxyphenyl | 144-146° | 471 | X |
| 33 | $CH_3$ | 4-biphenyl | 139.5°-142 | 517 | X |

*½ hydrate
**¼ hydrate

EXAMPLE 10

6-(4-Chlorophenyl)-4,6-dioxo-2-spirocyclopentylhexanoic acid (34)

The general procedure described in ORTH 460 for the synthesis of 6-aryl-4,6-diketohexanoic acids was followed for the synthesis of compound 34. To a reaction vessel containing anhydrous THF (250 ml) and diisopropylamine (14 ml, 0.1 Mole) stirring under nitrogen at 0° C. was added by syringe, n-BuLi (1.6 M, 62.5 ml, 0.1 Mole). The vessel was then cooled to −78° C. Alternatively, lithium hexamethyldisilazide (0.1 Mole) may be employed as the base in place of lithium diisopropylamide.

4-Chloroacetophenone (0.1 Mole) in anhydrous THF (50 ml) was added and the resulting solution allowed to stir for 30 minutes at −78° C. and cyclopentane-1-carboxy-1-acetic acid anhydride* (6.16 g, 0.04 Mole) in THF (100 ml) was added via syringe. The solution was allowed to stir for 1 hr at −78°, warmed to rt for 1 hr and poured into 5% HCl (250 ml). The mixture was extracted with $Et_2O$ (2×300 ml) and the combined ether extract was extracted with 10% NaOH (100 ml). The NaOH layer was separated and acidified with 4N HCl, and reextracted with $Et_2O$ (2×300 ml). The combined ether layers were dried ($Na_2SO_4$), filtered and concentrated in vacuo. The resultant residue was chromatographed and recrystallized from $CH_2Cl_2$: hexane to give the title compound 34 and 6-(4-Chlorophenyl)-4,6-dioxo-3-spirocyclopentyl hexanoic acid (35). Compound 34: mp=103°-104.5° C., MS, m/e 308 ($M^+$).

Anal. Calcd. for $C_{16}H_{17}O_4Cl$: C, 62.24; H, 5.55

Found: C, 62.59; H, 5.72

Compound 35; mp=108°-110° C., MS, m/e 308 ($M^+$)

Anal. Calcd. for $C_{16}H_{17}O_4Cl$: C, 62.24; H, 5.55

Found: C, 62.42; H, 5.58

The following diketo acids were obtained following the procedure of Example 10 by substituting either cyclohexane-1-carboxy-1-acetic acid anhydride or cycloheptane-1-carboxy-1-acetic acid anhydride* for cyclopentane-1-carboxy-1-acetic acid anhydride.

*Synthesized according to Scott, K. R. et al., J. of Pharm. Sci., 72, 183 (1983), see also I. Vogel, J. Chem. Soc. 2010, 1928.

6-(4-Chlorophenyl)-4,6-dioxo-2-spirocyclohexylhexanoic acid (36).

6-(4-Chlorophenyl)-4,6-dioxo-3-spirocyclohexyl hexanoic acid (37).

6-(4-Chlorophenyl)-4,6-dioxo-2-spirocycloheptyl hexanoic acid (38).

6-(4-Chlorophenyl)-4,6-dioxo-3-spirocycloheptyl hexanoic acid (39).

Compound 36; MS, m/e 322 ($M^+$); NMR ($CDCl_3$) δ 1.14–2.18 (10H, m), 2.73 (2H, s, $C_3$—H), 6.11 (1H, s), 7.26 (1H, s), 7.33–7.97 (4H,m).

Compound 37: NMR ($CDCl_3$) δ 1.08–2.10 (10H, m), 2.41 (2H, s, $C_2$—H), 6.32 (1H, s), 7.14 (1H, s), 7.33–7.93 (4H, m).

Compound 38; mp 135°–136° C., MS, m/e 336 ($M^+$).
Anal. Calcd. for $C_{18}H_{21}ClO_4$: C, 64.19, H, 6.28
Found: C, 64.06, H, 6.29

Compound 39; MS, m/e 336 ($M^+$); NMR ($CDCl_3$) δ 1.3–2.2 (12H, m), 2.57 (2H, s, $C_2$—H), 6.28 (1H, s), 7.28 (1H, s), 7.34–7.94 (4H, m).

EXAMPLE 11

3-[5-(4-Chlorophenyl)-1-(4-methoxyphenyl)-3-pyrazolyl]-N-hydroxy-2-spirocyclohexyl-N-methylpropanamide (40)

Compound 40 and the compounds of Table 4 were synthesized by the general procedure below described in ORTH 460.

A mixture of the appropriate 6-aryl-4,6-diketo-2-cycloalkyl-hexanoic acid (0.1 Mole) from Example 10 in methanol (750 ml) containing $Et_3N$ (0.2 Mole) was treated with 4-methoxyphenylhydrazine hydrochloride (17.4 g, 0.1 Mole) at rt for 1 hr. If the reaction was incomplete at this point, it was refluxed until complete. The resulting darkened solution was evaporated in vacuo and taken up in $Et_2O$ (700 ml); the ether solution was washed with aqueous 1N HCl (350 ml), brine, dried ($Na_2SO_4$), decolorized, evaporated in vacuo and recrystallized from $Et_2O$ to give the crude pyrazole propionic acids.

To a solution of the above acid(s) (2.77 mM) in tetrahydrofuran (20 ml) at 0° C., was added one drop of dimethyl formamide and oxalyl chloride (0 29 ml, 33 mM). After 0.5 hr the cooling bath was removed and stirring was continued for an additional 0.5 hr. The reaction mixture was concentrated in vacuo to remove any excess oxalyl chloride, and the acid chloride was taken up into THF (10 ml).

To a solution of methylhydroxylamine hydrochloride (0.35 g, 4.16 mM) and triethylamine ($Et_3N$) (1.55 ml, 11.10 mM) in THF, $H_2O$ (10 ml:5 ml) at 0° C., was added the THF solution of the acid chloride dropwise over a 5 minute period. The cooling bath was removed, and the reaction mixture was stirred for 1 hr, diluted to 100 ml with EtOAc, washed with $H_2O$, dried ($MgSO_4$), filtered, and concentrated in vacuo. Chromatography (silica gel) of the residue with EtOAc as eluent, followed by recrystallization from $CH_2Cl_2$:hexane gave the compounds of Table 4.

TABLE 4

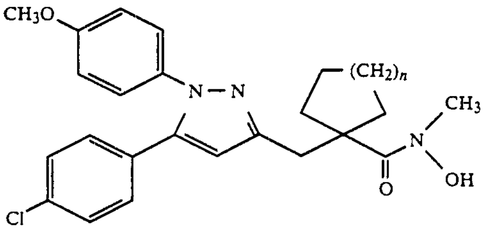

Compound Melting MS

TABLE 4-continued

| # | n | Point | m/e ($M^+$) | C,H,N |
|---|---|---|---|---|
| 40 | 2 | 150–151° | 453 | X |
| 41 | 1 | foam | 439 | X* |
| 42 | 3 | 149–151° | 467 | X** |

*¼ hydrate
**hydrate

Following the procedure of Example 11, but substituting compounds 35, 37 or 39 for the 6-aryl-4,6-diketo-2-cycloalkyl-hexanoic acid gave the corresponding 3-[5-(4-chlorophenyl)-1-(4-methoxyphenyl)-3-pyrazolyl]-N-hydroxy-2 -spirocycloalkyl-N-methylpropanamide.

EXAMPLE 12

6-(4-Chlorophenyl)-2.2-dimethyl-4,6-dioxohexanoic acid (43)

Following the procedure of Example 10, but substituting 2,2-dimethyl succinic anhydride for cyclopentane-1-carboxy-1-acetic acid anhydride and carrying out the reaction on 0.5 times the scale afforded a crude oil which upon recrystallization from $Et_2O$ (3×) afforded the title compound 43. mp=137°–139° C., MS, m/e 282 ($M^+$).

Anal. Calcd. for $C_{14}H_{15}ClO_4$: C, 59.47; H, 5.35
Found: C, 59 29; H, 5.21

The mother liquors from above contained the corresponding 6-(4-chlorophenyl)-3,3-dimethyl-4,6-dioxohexanoic acid (44) as the major component.

EXAMPLE 13

3-[5-(4-Chlorophenyl)-1-(4-methoxyphenyl)-3-pyrazolyl]-N-hydroxy-2,2,N-trimethylpropanamide (47)

Following the procedure of Example 11, and employing the isomeric mixture of geminal dimethyl diones 43 and 44 obtained in Example 12 afforded a mixture of four isomeric propionic acids which were separated by chromatography to afford 3-[5-(4-chlorophenyl)-1-(4-methoxyphenyl)-3-pyrazolyl]-2,2-dimethyl propionic acid (45), NMR (DMSO-$d_6$) δ 2.8 (s, $C_3$—H); MS, m/e 384 ($M^+$), and 3-[3-(4-chlorophenyl)-1-(4-methoxyphenyl)-5-pyrazolyl]-2,2-dimethyl propionic acid (46), mp=172°–174°, MS, m/e 384 ($M^+$).

Anal. Calcd. for $C_{21}H_{21}ClN_2O_3$: C, 65.54;H, 5.50;N, 7.28
Found: C, 65.48;H, 5.52;N, 7.40

The corresponding 3,3-dimethyl propionic acid analogs of compounds 45 and 46 were shown to be present (NMR) but were not purified.

A mixture of the 4 isomeric propionic acids was then converted to the corresponding N-methyl hydroxamic acids following the procedure described in Example 11. The crude product, which was shown (NMR) to contain 4 isomeric N-methyl hydroxamic acids, upon flash chromatography on Silica gave the title compound 47 as a yellow foam; NMR ($CDCl_3$) δ 3.05 (s, 2H, $C_3$—H), 6.33 (s, 1H, $C_{4'}$—H); MS, m/e 413 ($M^+$).

Anal. Calcd. for $C_{22}H_{24}ClN_3O_3$: C, 63.84;H, 5.85;N, 10.15
Found: C, 63.56;H, 5.91;N, 9.89

3-[5 (4-Chlorophenyl)-1-(4-methoxyphenyl)-3-pyrazolyl]-N-hydroxy-3,3,N-trimethylpropanamide (48) was obtained by chromatography as a yellow foam, NMR ($CDCl_3$) δ 2.89 (s, 2H, $C_2$—H), 6.38 (s, 1H, $C_{4'}$—H); MS, m/e 413 ($M^+$).

Anal. Calcd. for $C_{22}H_{24}ClN_3O_3$: C, 63.84; H, 5.85; N, 10.15

Found: C, 63.78; H, 5.81; N, 10.02

EXAMPLE 14

Sodium 1-(4-chlorophenyl)-4-methyl-6-hydroxyhexane-1,3-dionate (49a)

4-Chloroacetophenone (15.4 g, 0.1 mole) was added to LDA (0.1 mol) in THF (400 ml) at −78° C. under nitrogen. The resulting solution was stirred for 15 minutes and 2-methylbutyrolactone (5 g, 0.05 moles) in THF (20 ml) was added by syringe and the reaction kept at −78° C. for 1 hr and then at rt for 2 hr. The reaction mixture was poured into 5% HCl (150 ml) and extracted with ether, the ether layer was treated with 1 NaOH and the resulting solid, the title compound 49, was filtered (4 g, 29%) as a white solid, mp=135°–140° C.

Anal. Calcd. for $C_{13}H_{14}ClNaO_3$: C, 56.43; H, 5.10

Found: C, 56.12; H, 5.28

The NaOH layer from above was then acidified with HCl and extracted with ether, the ether layer dried ($Na_2SO_4$) and evaporated in vacuo to give a yellow semi-solid (3.6 g, 28%) which was 1-(4-chlorophenyl)-4-methyl 6-hydroxyhexane-1,3-dione (49b).

EXAMPLE 15

5-(4-Chlorophenyl)-3-(3-hydroxy-1-methylpropyl)-1-(4-methoxy phenyl)pyrazole (50)

Following the procedure described in Example 11, but employing 49b (2.54 g, 0.01 mole) as the diketo component afforded the title compound 50 as a white solid (1.1 g, 31%, Recry./$Et_2O$), mp=97.5°–98.5°; MS, m/e 356 (M+).

Anal. Calcd. for $C_{20}H_{21}ClN_2O_2$: C, 67.31; H, 5.93; N, 7.85

Found: C, 67.22; H, 6.30;5N, 7.85

EXAMPLE 16

3-[5-(4-Chlorophenyl)-1-(4-methoxyphenyl)-3-pyrazolyl]-3,N-dimethyl-N-hydroxypropanamide Hemihydrate (51)

To a solution of compound 50 (0.65 g, 1.8 mM) in acetone (50 ml) was added Jones Reagent (1.85 ml, 3.7 mM) and the reaction stirred for 1.5 hr, the acetone decanted and the chromium residues washed exhaustively with acetone. The combined acetone layers were then evaporated in vacuo, the residue dissolved in EtOAc (100 ml), washed ($H_2O$), dried ($Na_2SO_4$) and concentrated to give an oil which was chromatographed on Silica (EtOAc/MeOH, 30% as eluent) to afford 3-[5-(4-chlorophenyl)-1-(4-methoxyphenyl)-3-pyrazolyl]-3-methylpropanoic acid (0.62 g, 92%) as a yellow semi-solid which was used without further purification and following the procedure of Example 11 was converted to the title hydroxamic acid 51 as a yellow foam (92%); NMR ($CDCl_3$) δ 1.50 (d, 3H, J=7Hz, $C_3$—$CH_3$); MS, m/e 399 (M+).

Anal Calcd. for $C_{21}H_{22}ClN_3O_3 \bullet \frac{1}{2}H_2O$: C,61.68;H,5.67;N,10.27

Found: C,61.72;H,5.58;N,9.82

EXAMPLE 17

3-[5-(4-Chlorophenyl)-1-(4-methoxyphenyl)-3-pyrazolyl]-2,N-dimethyl-N-hydroxy propanamide Hemihydrate (52)

Following the procedure described in Example 14, but substituting 3-methylbutyrolactone for 2-methylbutyrolactone and employing the resulting product as the starting material for Examples 15 and 16 afforded the title compound 52 as a yellow foam (93%); NMR ($CDCl_3$) δ 1.25 (d, 3H, J=7Hz, $C_2$—$CH_3$); MS, m/e 399 (M+).

Anal. Calcd. for $C_{21}H_{22}ClN_3O_3 \bullet \frac{1}{2}H_2O$: C,61.68;H,5.67;N,10.27

Found: C,61.97;H,5.72;N,10.00

EXAMPLE 18

1-(4-Chlorophenyl)-3-(2-carboxyphenyl)propane-1,3-dione (53)

Following the general procedure described in Example 10 but substituting phthalic anhydride for cyclopentane-1-carboxy-1-acetic acid anhydride afforded the title compound as a white solid, mp=148°–150° C., MS, m/e 302 (M+).

Anal. Calcd. for $C_{16}H_{11}ClO_4$: C, 63.48; H, 3.66

Found: C, 63.33; H, 3.61

Likewise when cis-1,2-cyclohexane dicarboxylic anhydride; trans-1,2-cyclohexanedicarboxylic anhydride; cis-1,2,3,6-tetrahydrophthalic anhydride; 3,4,5,6-tetrahydrophthalic anhydride; 3,6-Endoxo-1,2,3,6-tetrahydrophthalic anhydride or 2,3-pyridinedicarboxylic anhydride were substituted for phthalic anhydride the following diketo acids were obtained.

cis-1-[1-(4-Chlorophenyl)-1,3-dioxoprop-3-yl]cyclohexane-2-carboxylic acid (54), white solid; mp=158°–160° C.; MS, m/e 308 (M+).

Anal. Calcd. for $C_{16}H_{17}ClO_4$: C, 62.24; H, 5.55

Found: C, 62.06; H, 5.77 trans-1-[1-(4-Chlorophenyl)-1,3-dioxoprop-3-yl]cyclohexane-2-carboxylic acid (55), white solid; mp=177°–180° C.; MS, m/e 308 (M+).

Anal Calcd. for $C_{16}H_{17}ClO_4$: C, 62.24; H, 5.55

Found: C, 62.02; H, 5.71 cis-1-[1-(4-Chlorophenyl)-1,3-dioxoprop-3-yl]cyclohex-4-ene-2-carboxylic acid (56), yellow crystalline solid, mp=132°–135° C.; MS, m/e 306 (M+).

Anal. Calcd. for $C_{16}H_{15}ClO_4$: C, 62.65; H, 4.92

Found: C, 62.50; H, 5.10

1-[3-(4-Chlorophenyl)-1,3-dioxopropyl]-2-carboxycyclohex-1-ene (57), white solid, mp=171°14 172° C.; MS, m/e 306 (M+).

Anal. Calcd. for $C_{16}H_{15}ClO_4$: C, 62.65; H, 4.92

Found: C, 62.25; H, 4.95 cis-1-[1-(4-Chlorophenyl)-1,3-dioxoprop-3-yl]-6-carboxy-2,5-endoxo-3,4-cyclohexene (58), white solid, mp=108°–109° C.; MS, m/e 320 (M+).

Anal. Calcd. for $C_{16}H_{13}ClO_5$: C, 59.92; H, 4.09

Found: C, 60.12; H, 4.13

1-(4-Chlorophenyl)-3-(6-carboxypyrid-2-yl)propan-1,3-dione (59), yellow solid, mp=183°–185° C.; MS, m/e 303 (M+).

Anal. Calcd. for $C_{15}H_{10}ClNO_4$: C, 59.32; H, 3.32; N, 4.61

Found: C, 59.00; H, 3.22; N, 4.57

In addition, when 4-methylacetophenone is substituted for 4-chloroacetophenone in Example 10 and either phthalic anhydride or cis-1,2-cyclohexanedicarboxylic anhydride is employed as the anhydride the following compounds are obtained.

1-(4-Methylphenyl)-3-(2-carboxyphenyl)propane-1,3-dione (60), white solid, mp=155°–157°; MS, m/e 282 (M+)

Anal. Calcd. for $C_{17}H_{14}O_4$: C, 72.33; H, 5.00

Found: C, 72.41; H, 5.01 cis-1-[1-(4-Methylphenyl)-1,3-dioxoprop-3-yl] cyclohexane-2-carboxylic acid (61), white solid, mp=144°-147°; MS, m/e 288 (M+).

Anal. Calcd. for $C_{17}H_{20}O_4$: C, 70.81; H, 6.99

Found: C, 70.39; H, 7.23

EXAMPLE 19

2-[5-(4-Chlorophenyl)-1-(4-methoxyphenyl)pyrazol-3-yl]-N-hydroxy-N-methylbenzamide Hemihydrate (62)

Following the procedure of Example 11 but employing 1-(4-Chlorophenyl)-3-(2-carboxyphenyl)propane-1,3-dione as the diketo acid afforded the title compound 62 as a white foam, MS, m/e 433 (M+).

Anal. Calcd. for $C_{24}H_{20}N_3O_3\bullet\frac{1}{2}H_2O$: C, 65.09; H,4.77; N,9.48

Found: C,64.66;H,4.63;N,9.13

Likewise, following the procedure of Example 11 but employing the diketo acids described in Example 18 afforded the following compounds.

cis-2-[5-(4-Chlorophenyl)-1-(4-methoxyphenyl)-3-pyrazolyl]-1-(N-hydroxy-N-methyl)carboxamidocyclohexane (63), white solid, mp=143°-145° C., MS, m/e 439 (M+).

Anal. Calcd. for $C_{24}H_{26}ClN_3O_3$: C, 65.52, H, 5.96, N, 9.55

Found: C, 65.26, H. 6.20, N, 9.29 cis-2-[5-(4-Chlorophenyl)-1-(4-methoxyphenyl)-3-pyrazolyl]-1-(N-hydroxy-N-methyl)carboxamidocyclohex-4-ene Hemihydrate (64), white foam, NMR ($CDCl_3$ δ 3.1 (s, 3H, $NCH_3$); MS, m/e 437 (M+).

Anal. Calcd. for $C_{24}H_{24}ClN_3O_3$: C, 64.49, H, 5.63, N, 9.40

Found: C, 64.76, H, 5.57, N, 9.06

Epimerization of compound 64 in base afforded trans-2-[5-(4-Chlorophenyl)-1-(4-methoxyphenyl)-3-pyrazolyl]-1-(N-hydroxy-N-methyl) carboxamidocyclohex-4ene Hemihydrate (65), white foam, NMR ($CDCl_3$) δ 3.3 (d, 3H, $NCH_3$); MS, m/e 437 (M+).

Anal. Calcd. for $C_{24}H_{24}ClN_3O_3$: C, 64.49; H, 5.63; N, 9.40

Found: C, 64.35; H, 5.58, N, 9.42 cis-1-[5-(4-Chlorophenyl)-1-(4-methoxyphenyl)-3-pyrazolyl]-6-(N-hydroxy-N-methyl)carboxamido-2,5-endoxo-3,4-cyclohexene (66), white solid, mp=108°-110° C., MS, m/e 451 (M+).

Anal. Calcd. for $C_{24}H_{22}ClN_3O_4$: C, 63.79; H, 4.91; N, 9.30

Found: C, 63.37; H, 4.96; N, 9.13

2-[5-(4-Chlorophenyl)-1-(4-methoxyphenyl)-3-pyrazolyl]-3 -(N-hydroxy-N-methylcarboxamido)pyridine (67), tan solid, mp=172°-175° C., MS, m/e 434 (M+).

Anal. Calcd. for $C_{23}H_{19}ClN_4O_3$: C, 63.52; H, 4.40; N, 12.88

Found: C, 63.40; H, 4.48; N, 12.81

2-[5-(4-Methylphenyl)-1-(4-methoxyphenyl)pyrazol-3-yl]-N-hydroxy-N-methylbenzamide Hemihydrate (68), white solid, mp=134°-136° C., MS, m/e 413 (M+).

Anal. Calcd. for $C_{25}H_{23}N_3O_3\bullet\frac{1}{2}H_2O$: C, 71.07; H, 5.72; N,9.94

Found: C, 71.20; H, 5.49; N,9.86 cis-2-[5-(4-Methylphenyl)-1-(4-methoxyphenyl)-3-pyrazolyl]-1-(N-hydroxy-N-methyl)carboxamidocyclohexane (69)

2-[5-(4-Chlorophenyl)-1-(4-methoxyphenyl)-3-pyrazolyl]-1 -(N-hydroxy-N-methyl)carboxamidocyclohex-1-ene (70)

EXAMPLE 20

3-Allyl-2.4-dimethoxypheneth-1-yl-4-methoxyphenylhydrazone Hemihydrate (71)

To a solution of 3-allyl-2,4-dihydroxyacetophenone [28.45 g, 0.148 mole; synthesized as described in J. Chem. Soc., pg 628 (1935)] in acetone (800 ml) was added potassium carbonate (442 g). The resulting slurry was treated with iodomethane (89 ml) at reflux for 6 hr, cooled and filtered, and the filtrate evaporated in vacuo and the crude product obtained was combined with that of an identical run and purified by flash chromatography on Silica to give 3-allyl-2,4-dimethoxyacetophenone (21.3 g), NMR ($CDCl_3$) δ 3.73, 3.9 (2s, 3H each, 2-, 4-$OCH_3$); MS, m/e 206 (M+).

A solution of 3-allyl-3,4-dimethoxyacetophenone (21.3 g, 97 mM) in EtOH (48.8 ml) and glacial Acetic Acid (3.25 ml) was treated with 4-methoxyphenylhydrazine (13.36 g, 97 mM) and heated at 35° C. for 1 hr and then allowed to stand at rt for 18 hr and the resulting solids filtered and washed with pet ether to afford pure 71 (15.04 g, 46%) as a yellow solid, mp=49°-50° C., MS, m/e 340 (M+).

Anal. Calcd. for $C_{20}H_{24}N_2O_3\bullet\frac{1}{2}H_2O$: C, 68.74; H, 7.21; N, 8.02

Found: C, 68.47; H, 7.17; N, 7.69

EXAMPLE 21

3-(3-Allyl-2,4-dimethoxyphenyl)-5-(4-chlorophenyl)-1-(4-methoxyphenyl)pyrazole (72)

A solution of compound 71 (12.26 9, 36 mM) in anhydrous THF (140 ml) was cooled to −10° C. under nitrogen and treated with n-BuLi (72 mM) to afford the dilithio anion which was allowed to stir at 0° C. for 0.5 hr. Methyl 4-chlorobenzoate (3.07 g, 18 mM) in THF (10 ml) was added to the above dianion and the reaction mixture stirred at 0° C. for 15 min, than neutralized with 3N HCl to a pH of 7.5, refluxed for 1 hr and stirred at rt for 21 hr. The reaction mixture was evaporated in vacuo to give a brown oil which was dissolved in $Et_2O$, washed ($H_2O$), dried and evaporated to give a dark brown oil which was purified by flash chromatography on Silica and crystallized from pet ether to give the title compound 72 (2.0 g, 24%) mp=44°-46° C., MS, m/e 460 (M+).

Anal. Calcd. for $C_{27}H_{25}ClN_2O_3$: C, 70.35; H, 5.47; N, 6.08

Found: C, 70.48; H, 5.62; N, 5.91

EXAMPLE 22

5-(4-Chlorophenyl)-3-[2,4-dimethoxy-3-(3-hydroxypropyl) phenyl]-1-(4-methoxyphenyl))pyrazole (73)

A slurry of compound 72 (6.82 g, 14.8 mm) in hexane was cooled to −10° C. under $N_2$ and treated with borane-methyl sulfide complex (10 mM) at 0° C. over a 0.5 hr period and then the reaction mixture refluxed gently for 2 hr, cooled and treated with 95% EtOH (12.75 ml) and 3N NaOH (1.59 ml) and cooled to 0° C., followed by the dropwise addition of 30% $H_2O_2$ (1.91 ml) and the refluxed for 0.5 hr, cooled and poured into ice water. The resulting solid was filtered to give crude alcohol (6.25 g) which was purified via flash column chromatography on Silica and recrystallization from $Et_2O$/pet ether to afford pure 73 (2.89 g) as a yellow solid, mp=152°-153° C.; MS, m/e 478 (M+).

Anal. Calcd. for $C_{27}H_{27}ClN_2O_4$: C, 67.70; H, 5.68; N, 5.85

Found: C, 67.95; H, 5.94; N, 5.73

EXAMPLE 23

3-[3-[5-(4-Chlorophenyl)-1-(4-methoxyphenyl)pyrazol-3-yl]-2,6-dimethoxyphenyl] propionic acid (74)

Following the procedure of Example 16, but substituting compound 73 for compound 50 afforded the title compound 74 as a white solid, mp=100°-101° C., MS, m/e 492 (M+).

EXAMPLE 24

3-[3-[5-(4-Chlorophenyl)-1-(4-methoxyphenyl)pyrazol-3-yl]-2,6-dimethoxyphenyl]-N-hydroxy-N-methyl-propanamide (75)

Following the procedure described in Example 11 for hydroxamic acid synthesis but employing compound 74 as the starting propionic acid afforded the title compound 75 which crystallized from EtOAc: hexane as a white solid with 0.5 mole of EtOAc as solvate, mp=90°-92° C., MS, m/e 521 (M+).

Anal. Calcd. for $C_{28}H_{28}ClN_3O_5 \bullet \frac{1}{2}C_4H_8O_2$: C, 63.65; H,5.70; N,7.42

Found: C,63.89;H,5.94;N,7.26

EXAMPLE 25

1-(4-Methoxyphenyl)-5-(4-methylphenyl)pyrazol-3-yl carboxaldehyde (76)

Pyridine (54.6 ml, 0.68 M) was dissolved in $CH_2Cl_2$ (450 ml), cooled to 0° C. and $CrO_3$ (33.8 g) was added with stirring. Compound 4 (17.68 g, 56.3 mM) dissolved in $CH_2Cl_2$ (350 ml) was added to the mixture with stirring and kept at 0° C. for 30 min, then warmed to RT for 7 hr. The solvent was decanted and filtered through Florisil. The residual black tar was sonicated with EtOAc (3×) and the combined organic layer was evaporated in vacuo to give a brown oil which was dissolved in $Et_2O$, washed with 10% NaOH, 4N HCl and saturated brine, dried ($Na_2SO_4$), filtered and evaporated in vacuo to give a tan solid which upon recrystallization from $Et_2O$:hexane afforded the title compound 76 as a white solid (14.5 g, 83%) mp=84°-86°.

Following the procedure of Example 25, but substituting 3-hydroxymethyl-1,5- bis(4-methoxyphenyl)-pyrazole, compound 88, for 3-hydroxymethyl-1-(4-methoxy-phenyl)-5-(4-methylphenyl)pyrazole afforded 1,5-bis(4-methoxyphenyl)pyrazole- 3-aldehyde, compound 89 as a white solid, mp 113°-115° C., MS, m/e 308 (M+).

Anal. Calcd. for $C_{18}H_{16}N_2O_3$: C, 70.12; H, 5.23; N, 9.09

Found: C, 70.06; H, 5.21; N, 9.04.

EXAMPLE 26

1-[1-(4-Methoxyphenyl)-5-(4-methylphenyl)-3-pyrazolyl]-1-phenyl-methanol (77)

Compound 76 (2.92 g, 10 mM) was dissolved in THF (100 ml) and cooled to 0° C. Phenylmagnesium bromide (11 mM) was added by syringe and after 1 hr the reaction was quenched with saturated $NH_4Cl$ (50 ml). $Et_2O$ (150 ml) was added and the organic layer was separated, washed (brine), dried ($Na_2SO_4$), filtered and evaporated in vacuo to afford the title compound 77 as a tan solid, mp=101°-103°; MS, m/e 370 (M+).

Anal. Calcd. for $C_{24}H_{22}N_2O_2$: C, 77.81; H, 5.99; N, 7.56

Found: C, 77.67; H, 6.13; N, 7.34

In a similar manner, substituting 4-fluorophenylmagnesium bromide for phenylmagnesium bromide affords 1-(4-fluorophenyl)-1-[1-(4-methoxyphenyl)-5- (4-methylphenyl)-3 -pyrazolyl] methanol 78 as a yellow foam; MS, m/e 388 (M+).

Anal. Calcd. for $C_{24}H_{21}FN_2O_2$: C, 74.20; H, 5.45; N, 7.21

Found: C, 73.80; H, 5.29; N, 7.17

In addition, substituting the appropriate arylmagnesium halide for phenylmagnesium bromide and employing either aldehyde 76 or 89 (Procedure A) afforded compounds of Table 5. Alternatively, substituting the appropriate aryl halide or the appropriately activated substituted aryl compound for phenylmagnesium bromide and subsequent treatment with butyl lithium at −78° C. followed by addition of aldehyde 76 or 89 (Procedure B) afforded the remaining compounds of Table 5.

EXAMPLE 27

3-Benzoyl-1-(4-methoxyphenyl)-5-(4-methylphenyl)-pyrazole (79)

Compound 77 (3.7 g, 10 mM) was dissolved in $CH_2Cl_2$ (100 ml) and pyridinium chlorochromate (3.44 g, 16 mM) was added with vigorous stirring and stirred for 30 min. $Et_2O$ (150 ml) was added and the mixture was sonicated for 5 min and filtered through florisil (100-200 mesh), the Florisil washed with additional $Et_2O$ and the combined $Et_2O$ layer evaporated in vacuo to yield the title compound of sufficient purity for subsequent steps.

TABLE 5

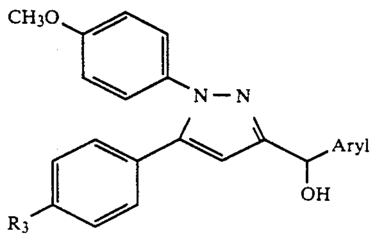

| Compound # | $R_3$ | Aryl | Melting Point | MS (m/e) M+ | Procedure | C,H,N |
|---|---|---|---|---|---|---|
| 90 | Me | 4-Biphenylyl | 135-137° | 446 | A | X |
| 91 | Me | 4-Chlorophenyl | 130-132° | 404 | A | X |
| 92 | Me | 4-Tolyl | 138-140° | 384 | A | X |

TABLE 5-continued

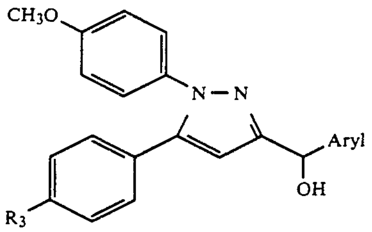

| Compound # | $R_3$ | Aryl | Melting Point | MS (m/e) $M^+$ | Procedure | C,H,N |
|---|---|---|---|---|---|---|
| 93 | Me | 1-Naphthyl | 156-159° | 420 | A | X* |
| 94 | Me | 2-Naphthyl | 142-143.5° | 420 | A | X |
| 95 | Me | 4-Methoxyphenyl | 109-110.5° | 400 | B | X |
| 96 | Me | 2-Thienyl | 134-136° | 376 | B | X |
| 97 | Me | 2-Methoxyphenyl | 109-111° | 400 | B | X |
| 98 | Me | 6-Methoxy-2-naphthyl | 170.5-172.5° | 450 | B | X** |
| 99 | Me | 2-Furyl | 127-130° | 360 | B | X |
| 100 | OMe | 4-Tolyl | 138-139° | 400 | A | X |
| 101 | OMe | 4-Chlorophenyl | 155-156° | 420 | A | X |
| 102 | OMe | 4-Methoxyphenyl | 148-149° | 416 | B | X |
| 103 | OMe | 2-Methoxy-5-bromophenyl | foam | 495 | B*** | X |
| 104 | OMe | 2-Methoxyphenyl | foam | 416 | B | X |
| 105 | OMe | Phenyl | 103-106° | 386 | A | X |
| 106 | OMe | 2,3-Dimethoxyphenyl | foam | 446 | B | X |

*½ hydrate
**¼ hydrate
***By-product in synthesis of compound 102

Recrystallization from $Et_2O$ affords 79 as a white solid, mp=166°-167°; MS, m/e 368 ($M^+$).

Anal. Calcd. for $C_{24}H_{20}N_2O_2$: C, 78.24; H, 5.47; N, 7.60

Found: C, 77.93; H, 5.29; N, 7.63

In a similar manner, substituting compound 78 for 77 afforded 3-(4-fluorobenzoyl)-1-(4-methoxyphenyl)-5-(4-methylphenyl) pyrazole (80) as a white solid, mp=138°-139°; MS, m/e 386 ($M^+$).

In addition, substituting the appropriate alcohol from Table 5 for compound 77 afforded the compounds of Table 6.

TABLE 6

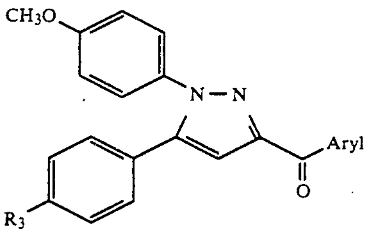

| Compound # | $R_3$ | Aryl | Melting Point | MS (m/e) $M^+$ | C, H, N |
|---|---|---|---|---|---|
| 107 | Me | 4-Biphenylyl | 146-148° | 444 | X |
| 108 | Me | 4-Chlorophenyl | 157-158.5° | 402 | X |
| 109 | Me | 4-Tolyl | 136-138° | 382 | X |
| 110 | Me | 1-Naphthyl | 158-159.5° | 418 | X |
| 111 | Me | 2-Naphthyl | 158.5-159.5° | 418 | X |
| 112 | OMe | 4-Tolyl | 137-138° | 398 | X |
| 113 | OMe | 4-Chlorophenyl | 145-147° | 418 | X |
| 114 | Me | 2-Thienyl | 161-162° | 374 | X |
| 115 | Me | 4-Methoxyphenyl | 127-128° | 398 | X |
| 116 | OMe | 4-Methoxyphenyl | 138-139° | 414 | X |
| 117 | Me | 2-Methoxyphenyl | 141-143° | 398 | X |
| 118 | OMe | 2-Methoxyphenyl | foam | 414 | X |
| 119 | Me | 6-Methoxy-2-naphthyl | 175-176° | 448 | X |

TABLE 6-continued

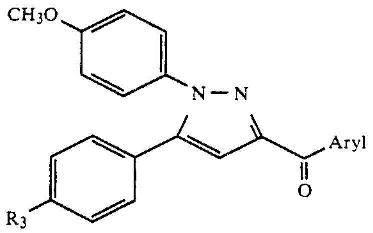

| Compound # | $R_3$ | Aryl | Melting Point | MS (m/e) $M^+$ | C, H, N |
|---|---|---|---|---|---|
| 120 | Me | 2-Furyl | 139.5-141° | 358 | X |
| 121 | OMe | 2,3-Dimethoxyphenyl | foam | 444 | X |

EXAMPLE 28

(E)-Ethyl-3-[1-(4-methoxyphenyl)-5-(4-methylphenyl)-3-pyrazolyl]-3-phenyl-2-propenoate (81) and the corresponding (Z) isomer (82)

Triethyphosphonoacetate (2.24 g, 10 mM) was dissolved in anhydrous THF (80 ml), cooled to −78° C. and n-BuLi (10 mM) was added by syringe and the resulting colorless solution stirred 45 min. Compound 79 (3.68 g, 10 mM) in THF (80 ml) was added by syringe, the resulting solution stirred at −78° for 15 min, warmed to RT and then allowed to reflux for 8 hr under a $N_2$ atmosphere. The reaction was cooled to RT, partitioned between $Et_2O$ and 5% HCl, and the $Et_2O$ layer washed with brine, dried ($Na_2SO_4$) and evaporated in vacuo to give an oil which was chromatographed on Silica (Hexane:15% EtOAc) to afford a 3:2 mixture of 81:82.

Compound 81, oil, NMR ($CDCl_3$)δ 6.35 (s, 1H) 6.53 (s, 1H).

Compound 82, white solid, mp=143°-144°; NMR ($CDCl_3$) δ 6.18 (s, 1H) 6.85 (s, 1H).

Anal. Calcd. for $C_{28}H_{26}N_2O_3$: C, 76.69; H, 5.98; N, 6.39

Found: C, 76.82; H, 6.00; N, 6.48

Following the above procedure but substituting Compound 80 for 79 afforded (E)-Ethyl 3-(4-fluorophenyl)-3-[1-(4-methoxyphenyl)-5-(4-methylphenyl) -3-pyrazolyl]-2-propenoate (83) and the corresponding (Z)-isomer (84).

Compound 83, oil, NMR ($CDCl_3$) δ 6.30 (s, 1H), 6.55 (s, 1H).

Compound 84, mp=132°-133° (prisms); NMR ($CDCl_3$) δ 6.20 (s, 1H), 6.88 (s, 1H).

Anal. Calcd. for $C_{28}H_{25}FN_2O_3$: C, 73.67; H, 5.52; N, 6.14

Found: C, 74.04; H, 5.53; N, 6.25

Following the procedure of Example 28, but substituting the appropriate ketone of Table 6 for compound 79 afforded the compounds of Table 7. The E and Z isomers were separated by flash chromatography on Silica.

EXAMPLE 29

Ethyl 3-[1-(4-methoxyphenyl)-5-(4-methylphenyl)-3-pyrazolyl]-3-phenyl propanoate (85)

Compound 81 (100 mg) was dissolved in EtOH (20 ml) and acetic acid (2 ml) and 10% palladium on carbon (50 mg) was added. The mixture was shaken on a Parr hydrogenator at 50 psi for 48 hr. The reaction mixture was filtered through celite and evaporated to give the title compound 85 as an oil, 100 mg. NMR ($CDCl_3$) δ 1.13 (3H, t, J=7 Hz) 2.30 (3H, s), 3.0 (1H, d, J=8 Hz; JAB=24 Hz), 3.33 (1H, d, J=8 Hz; JAB=24 Hz), 3.79 (3H, s), 4.05 (2H, g, J=7 Hz), 4.65 (1H, t, J=8 Hz), 6.17 (1H, s), 6.82 (2H, d), 7.04 (4H, s), 7.06-7.50 (7H, m).

Following the above procedure, but substituting Compound 82 for 81 also affords compound 85.

Following the procedure of Example 29, but substituting the appropriate ester from Table 7 for compound 81 afforded the compounds of Table 8.

TABLE 7

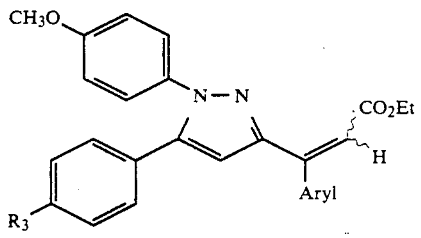

| Compound # | $R_3$ | Aryl | E/Z Isomers | Melting Point | MS (m/e)M+ | C, H, N |
|---|---|---|---|---|---|---|
| 122 | OMe | 4-tolyl | E | foam | 468 | X |
| 123 | OMe | 4-tolyl | Z | 211-214° | 468 | X |
| 124 | Me | 4-tolyl | E | foam | 452 | X |
| 125 | Me | 4-tolyl | Z | 118-119° | 452 | X |
| 126 | OMe | 4-chlorophenyl | E | foam | 488 | X |
| 127 | OMe | 4-chlorophenyl | Z | 126-127° | 488 | X |
| 128 | Me | 4-chlorophenyl | Z | 141-143° | 472 | X |
| 129 | Me | 4-chlorophenyl | E | foam | 472 | X |
| 130 | OMe | 4-methoxyphenyl | E | foam | 484 | X |
| 131 | OMe | 2-methoxyphenyl | E/Z[a] | foam | 484 | X |
| 132 | Me | 4-biphenylyl | Z | 147-149° | 514 | X |
| 133 | Me | 4-biphenylyl | E | foam | 514 | X |
| 134 | Me | 1-naphthyl | E/Z[b] | foam | 488 | X |
| 135 | Me | 2-naphthyl | Z | 171-172.5° | 488 | X |
| 136 | Me | 2-naphthyl | E | 123-125.5° | 488 | X |
| 137 | Me | 2-methoxyphenyl | E/Z[c] | foam | 468 | X |
| 138 | Me | 4-methoxyphenyl | E | foam | 468 | X |
| 139 | Me | 4-methoxyphenyl | Z | 104-107° | 468 | X |
| 140 | Me | 2-thienyl | E | foam | 444 | X |
| 141 | Me | 2-thienyl | Z | 121.5-122.5° | 444 | X |
| 142 | Me | 6-methoxy-2-naphthyl | E | foam | 518 | X |
| 143 | Me | 6-methoxy-2-naphthyl | Z | 125-127° | 518 | X |
| 144 | Me | 2-furyl | E | foam | 428 | X |
| 145 | Me | 2-furyl | Z | foam | 428 | X[e] |
| 146 | OMe | 2,3-dimethoxyphenyl | E/Z[d] | foam | 514 | X |

[a]E:Z ratio of 5:1
[b]E:Z ratio of 5:4
[c]E:Z ratio of 1:1
[d]E:Z ratio of 1:3
[e]½ hydrate

TABLE 8

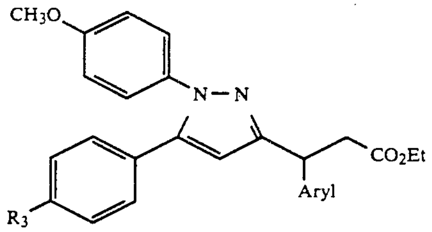

| Compound # | Aryl | Melting Point | MS (m/e)M+ | C, H, N |
|---|---|---|---|---|
| 147 | 4-biphenylyl | foam | 516 | X |
| 148 | 4-methylphenyl | oil | 454 | X |
| 149 | 4-chlorophenyl | glass | 474 | X |
| 150 | 1-naphthyl | foam | 490 | X |

EXAMPLE 30

3-[1-(4-Methoxyphenyl)-5-(4-methylphenyl)-3-pyrazolyl]-3-phenyl propanoic acid (86)

Following the procedure of Example 8, but substituting Compound 85 for 7 afforded the title compound 86, NMR ($CDCl_3$) δ 2.32 (3H, s), 2.8–3.7 (2H, ABX complex), 3.8 (3H, s), 4.64 (1H, t, J=7 Hz), 6.18 (1H, s), 6.81 (2H, d), 7.04 (4H, s), 7.0–7.5 (7H, m).

Following the procedure of Example 8, but substituting the appropriate propanoate ester of Table 8 for compound 7 afforded the compounds of Table 9.

TABLE 9

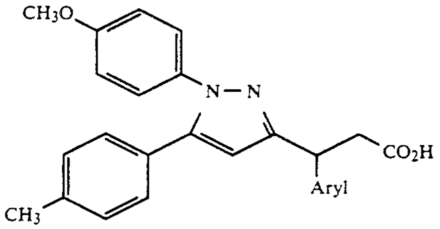

| Compound # | Aryl | Melting Point | MS (m/e)M+ | C, H, N |
|---|---|---|---|---|
| 151 | 4-fluorophenyl | 185–186° | 430 | X |
| 152 | 4-biphenylyl | 255–256° | 488 | X* |
| 153 | 4-chlorophenyl | 173–175° | 446 | X |
| 154 | 4-tolyl | 158–160° | 426 | X |

*½ hydrate

Following the procedure of Example 8, but substituting the appropriate propenoate esters of Table 7 for compound 7 afforded the compounds of Table 10.

TABLE 10

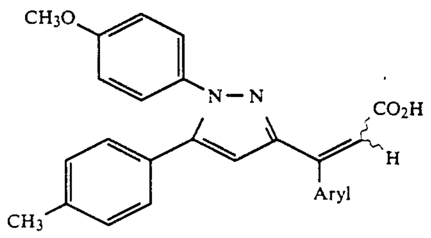

| Compound # | Aryl | E/Z Isomers | Melting Point | MS (m/e)M+ | C, H, N |
|---|---|---|---|---|---|
| 155 | phenyl | E | foam | 410 | X |
| 156 | 4-fluorophenyl | Z | 240–241° | 428 | X |

TABLE 10-continued

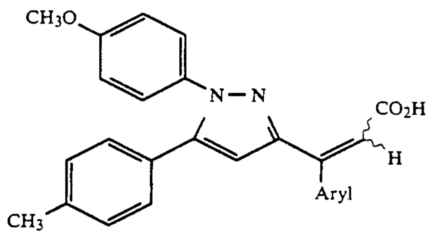

| Compound # | Aryl | E/Z Isomers | Melting Point | MS (m/e)M+ | C, H, N |
|---|---|---|---|---|---|
| 157 | 4-chlorophenyl | E | foam | 444 | X |
| 158 | 4-chlorophenyl | Z | 252–254° | 444 | X |
| 159 | 4-biphenylyl | Z | 151–152° | 486 | X |
| 160 | 4-tolyl | Z | 150.5–153° | 424 | X |

EXAMPLE 31

3-[1-(4-methoxyphenyl)-5-(4-methylphenyl)-3-pyrazolyl]-3-phenyl-N-hydroxy-N-methylpropanamide (87)

Following the procedure of Example 9, but substituting Compound 86 for 18 afforded the title compound 87, NMR ($CDCl_3$) δ 2.31 (3H, s), 3.18 (3H, s), 2.8–3.7 (2H, ABX complex), 3.81 (3H, s), 4.64 (1H, t, J=7 Hz), 6.19 (1H, s), 6.82 (2H, d), 7.04 (4H, s), 7.04–7.5 (7H, m).

EXAMPLE 32

3-Biphenylyl-N-hydroxy-3-[1-(4-methoxyphenyl)-5-(4-methylphenyl)-3-pyrazolyl]-N-methylpropanamide hemihydrate (161)

Following the procedure of Example 9, but substituting Compound 152 for 18 afforded the title compound 161 as a tan solid, mp=155.5°–157.5°; MS (m/e) 517(M+).

Anal Calcd. for $C_{33}H_{31}N_3O_3$ ↑ ½$H_2O$: C, 75.26; H, 6.12; N, 7.98

Found: C, 75 23; H, 6.10; %, 7 92.

In addition, following the procedure of Example 9, but substituting the appropriate propenoic acid from Table 10 for 18 afforded the compounds of Table 11.

TABLE 11

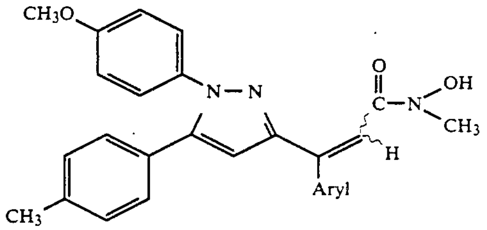

| Compound # | Aryl | E/Z Isomers | Melting Point | MS (m/e)M+ | C, H, N |
|---|---|---|---|---|---|
| 162 | phenyl | E | 137–139 | 439 | X |
| 163 | 4-fluorophenyl | E | foam | 457 | X[1] |
| 164 | 4-chlorophenyl | E | foam | 473 | X |
| 165 | 4-chlorophenyl | Z | 111–115° | 473 | X[2] |
| 166 | 4-biphenylyl | Z | 167–169° | 515 | X |
| 167 | 4-fluorophenyl | Z | foam | 457 | X[1] |
| 168 | 4-biphenylyl | E | 209–210° | 515 | X |

[1] ¼ hydrate
[2] ½ hydrate

IN VIVO ALLEVIATION OF INFLAMMATION

Polyarthritis was induced in Lewis strain laboratory rats (weight=about 200 grams) by injection of a suspension of *Mycobacterium butyricum* in mineral oil into the subplantar tissue of the mammal's hind paws. On day 10 after the injection, the rats were assigned to groups, and paw volumes and body weights were recorded. Paw volumes of the contralateral, uninjected hind paw were determined by mercury plethylsmography. Per oral (p.o.) dosing began and continued for five consecutive days thereafter. On day 14 after the initial injection, approximately four hours after the final dose was administered, paw volumes and body weights were recorded and quantitated.

Anti-inflammatory activity of the N-hydroxypropanamide pyrazole compounds is expressed as the percent inhibition of paw volume increase. The results of this study for several compounds of the structure shown below are shown in Table 12, hereinafter.

TABLE 12

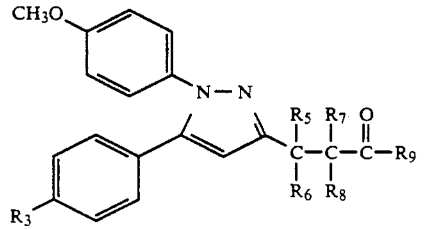

| % INH. No. | $R_3$ | $R_5$ | $R_6$ | $R_7$ | $R_8$ | $R_9$ | % INH. p.o. (mpk) |
|---|---|---|---|---|---|---|---|
| 8 | Cl | H | H | Phenyl | H | OEt | 61% @10 |
| 18 | Cl | H | H | 4-Chlorophenyl | H | CH | 39% @10 |
| 23 | Me | H | H | 2-Methoxyphenyl | H | OH | 23% @25 |
| 26 | Cl | H | H | 4-Chlorophenyl | H | N(OH)Me | 13% @10 |
| 42 | Cl | H | H | spirocycloheptyl | — | N(OH)Me | 17% @10 |
| 47 | Cl | H | H | Me | Me | N(OH)Me | 17% @10 |
| 51 | Cl | Me | H | H | H | N(OH)Me | 40% @8 |
| 52 | Cl | H | H | Me | H | N(OH)Me | 45% @15 |
| 62 | Cl | — | — | Phenyl | — | N(OH)Me | 37% @15 |
| 63 | Cl | — | — | cis-Cyclohexyl | — | N(OH)Me | 29% @10 |
| 151 | Me | * | H | H | H | OH | 48% @10 |
| 161 | Me | ** | H | H | H | N(OH)Me | 10% @10 |
| | | | | STRUCTURE II (X = OME) | | | |
| 75 | Cl | H | H | H | H | N(OH)Me | 20% @15 |

*4-Fluorophenyl
**4-Biphenylyl

The following pyrazoles are described in the invention and the percent inhibition of paw volume increase for each is shown below.

| No. | % INH., p.o. (mpk) |
|---|---|
| 92 | 27% @ 10 |
| 94 | 29% @ 10 |
| 105 | 49% @ 15 |
| 108 | 25% @ 10 |
| 155 | 62% @ 10 |
| 157 | 24% @ 10 |
| 164 | 22% @ 10 |

II. EX VIVO ARACHIDONIC ACID METABOLISM OF RAT PLEURAL EXUDATE CELLS

This assay determines the ability of orally administered compounds to inhibit arachidonic acid metabolism with rat pleural exudate cells, via the lipoxygenase and/or cyclooxygenase enzymes. Sprague-Dawley rats (250–275 gm) are fasted overnight. The next morning, an acute inflammatory response is induced by the intrathoracic injection of 1 ml of 0.25% carrageenan. Three hours later the rats are dosed orally with the test compounds at a screening dose of 16.5–30 mpk. Thirty minutes to one hour later the rats are sacrificed and pleural fluid harvested. The exudate fluids are diluted 1:5 using Hanks BSS and stimulated using 10 μ/ml calcium ionophore A-23187. The reaction is stopped after 15 minutes by the addition of 25 μl of 1N HCl, and the samples are centrifuged at 1000 g to sediment the cells. The supernate is extracted and applied to a C-18 HPLC column. The arachidonic acid metabolites 12-HHT (cyclooxygenase), 5-HETE, and leukotriene $B_4$ (lipoxygenase) are eluted using an acetonitrile methanol gradient and detected by UV absorption at 235 and 270 nm.

The percent inhibition of the arachidonic acid metabolites is indicative of the anti-inflammatory activity of the tested compound and the results of this method for several compounds of the invention are listed in Table 13. The values shown are the percent inhibition at the dose indicated except for the those cases in which the $IC_{50}$ value is given

TABLE 13

| No. | % INH., p.o. Lipoxygenase (mpk) | % INH., p.o. Cyclooxygenase (mpk) |
|---|---|---|
| 109 | 62% @ 30 | 94% @ 30 |
| 132 | 34% @ 16.5 | 54% @ 16.5 |
| 125 | $IC_{50}$ = 9 mpk | $IC_{50}$ = 14 mpk |
| 150 | 42% @ 30 | 6% @ 30 |
| 158 | 53% @ 17.5 | 32% @ 17.5 |
| 163 | $IC_{50}$ = 10 mpk | $IC_{50}$ = 1 mpk |
| 165 | 12% @ 30 | 55% @ 30 |
| 168 | 3% @ 30 | 39% @ 30 |

What is claimed is:

1. A compound of the formula

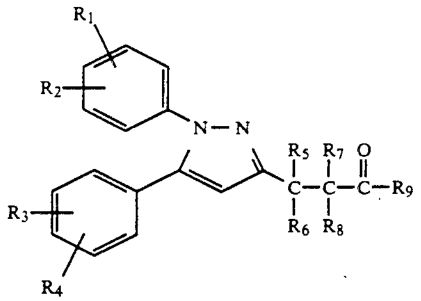

wherein $R_1$, $R_2$, $R_3$ and $R_4$ are the same or different and are individually selected from the group consisting of hydrogen, lower alkyl, lower alkoxy, amino, acetamido, phenyl, halo, hydroxy, lower alkylsulfonyl, lower alkylthio, nitro, trifluoromethyl, ω-trifluoromethyl lower alkoxy, or $R_1R_2$ or $R_3R_4$ taken together with the phenyl group to which they are attached, form a naphthyl or substituted naphtyl group wherein the substituent is halo, lower alkyl or lower alkoxy; $R_5$, and $R_7$ are the same or different and are individually selected from the group consisting of hydrogen, lower alkyl; $R_6$ and $R_8$ taken together are part of a ring selected from the group consisting of a cyclohexyl, cyclohexenyl and a 7-oxobicyclo [2.2.1] heptenyl ring, $R_9$ is selected from hydroxy, $—OR_{10}$ or $—N(OH)R_{10}$ wherein $R_{10}$ is lower alkyl; and the pharmaceutically acceptable salts thereof.

2. A compound of claim 1 wherein $R_1$ and $R_3$ are selected from the group consisting of halo, lower alkyl and lower alkoxy; and $R_2$ and $R_4$ are hydrogen.

3. A compound of claim 1 which is selected from cis-2-[5-(4-chlorophenyl)-1-(4-methoxyphenyl)-3-pyrazolyl]-1-(N-hydroxy-N-methyl)-carboxamidocyclohexane.

* * * * *

UNITED STATES PATENT AND TRADEMARK OFFICE
CERTIFICATE OF CORRECTION

PATENT NO. : 5,051,518

DATED : September 24, 1991

INVENTOR(S) : Murray, et al.

It is certified that error appears in the above-identified patent and that said Letters Patent is hereby corrected as shown below:

Col. 40, line 2, the word "naphtyl" should be --naphthyl--

Signed and Sealed this

Twenty-ninth Day of June, 1993

Attest:

Michael K. Kirk

MICHAEL K. KIRK

*Attesting Officer* *Acting Commissioner of Patents and Trademarks*